US012573502B2

(12) United States Patent
Chamberlain et al.

(10) Patent No.: US 12,573,502 B2
(45) Date of Patent: Mar. 10, 2026

(54) ULTRASOUND UTILITY STATION

(71) Applicant: FUJIFILM SONOSITE, INC.,
Bothell, WA (US)

(72) Inventors: Craig Chamberlain, Bothell, WA (US);
Andrew Lundberg, Bothell, WA (US);
Patrick Nally, Bothell, WA (US); **Kenji
Kimura, Bothell, WA (US); Trevor
Rogers, Bothell, WA (US); Tyler
Dawson, Bothell, WA (US); Saeed
Aliakbari, Bothell, WA (US); Davin
Dhatt**, Bothell, WA (US)

(73) Assignee: FUJIFILM SONOSITE, INC.,
Bothell, WA (US)

( * ) Notice: Subject to any disclaimer, the term of this
patent is extended or adjusted under 35
U.S.C. 154(b) by 0 days.

(21) Appl. No.: 18/507,144

(22) Filed: Nov. 13, 2023

(65) Prior Publication Data

US 2024/0079123 A1      Mar. 7, 2024

Related U.S. Application Data

(63) Continuation of application No. 17/710,422, filed on
Mar. 31, 2022, which is a continuation of application
No. 17/693,089, filed on Mar. 11, 2022.

(51) Int. Cl.
G16H 40/40        (2018.01)
A61B 8/00         (2006.01)
                    (Continued)
(52) U.S. Cl.
CPC ........... G16H 40/40 (2018.01); A61B 8/4281
(2013.01); A61B 8/4433 (2013.01);
(Continued)

(58) Field of Classification Search
None
See application file for complete search history.

(56) References Cited

U.S. PATENT DOCUMENTS 4,031,449 A * 6/1977 Trombly ............... H02J 50/005
                                              320/108
6,117,085 A    9/2000 Picatti et al.
                    (Continued)

FOREIGN PATENT DOCUMENTS

CN        203829207 U    9/2014
EP         1923001 A1    5/2008
                    (Continued)

OTHER PUBLICATIONS

Machine generated English Translation of JP 2005-198761 (Year:
2005).
                    (Continued)

*Primary Examiner* — Katherine L Fernandez
(74) *Attorney, Agent, or Firm* — Womble Bond Dickinson
(US) LLP

(57)          ABSTRACT

Embodiments of ultrasound utility station and methods for
using the same are disclosed. In some embodiments, the
method includes displaying a status of the ultrasound
machine that indicates a location of the ultrasound machine
and an amount of charge of a battery of the ultrasound
machine, and displaying an additional status that indicates
an additional location of the ultrasound utility station and
one or more available ultrasound probes on the ultrasound
utility station. After receiving a selection of an ultrasound
probe of the available ultrasound probes and a user input that
determines a schedule for said configuring the ultrasound
machine, the method instructs the ultrasound utility station
to charge the battery of the ultrasound machine and provide
the ultrasound probe for transfer to the ultrasound machine.

17 Claims, 6 Drawing Sheets

(51) Int. Cl.
　　*G01C 21/00*　　　(2006.01)
　　*G06V 10/764*　　 (2022.01)
　　*G16H 40/20*　　　(2018.01)

(52) U.S. Cl.
　　CPC .............. *A61B 8/4472* (2013.01); *A61B 8/56*
　　　　(2013.01); *A61B 8/565* (2013.01); *G01C*
　　　　*21/383* (2020.08); *G06V 10/764* (2022.01);
　　　　*G16H 40/20* (2018.01); *A61B 8/465* (2013.01);
　　　　　　　　　　　　　　*A61B 8/467* (2013.01)

(56)　　　　　　References Cited

U.S. PATENT DOCUMENTS

| | | | |
|---|---|---|---|
| 6,764,373 B1 | 7/2004 | Osawa | |
| 7,166,987 B2 | 1/2007 | Lee et al. | |
| 7,867,168 B2* | 1/2011 | Little | G01S 7/52082 |
| | | | 600/463 |
| 8,352,114 B2 | 1/2013 | More et al. | |
| 8,398,408 B1* | 3/2013 | Hansen | A61B 8/4405 |
| | | | 320/109 |
| 9,237,634 B2 | 1/2016 | Knibbe et al. | |
| 9,487,101 B2 | 11/2016 | Kees et al. | |
| 9,632,505 B2 | 4/2017 | Hickerson et al. | |
| 9,763,644 B2 | 9/2017 | Pelissier et al. | |
| 10,224,745 B2 | 3/2019 | Easton et al. | |
| 10,279,488 B2 | 5/2019 | Li et al. | |
| 10,367,369 B2 | 7/2019 | Partovi et al. | |
| 10,486,742 B2 | 11/2019 | Solar | |
| 10,875,414 B2 | 12/2020 | Partovi et al. | |
| 10,919,163 B1 | 2/2021 | Li et al. | |
| 11,745,605 B1 | 9/2023 | Li et al. | |
| 11,908,566 B2 | 2/2024 | Roh et al. | |
| 11,984,731 B2 | 5/2024 | Makwinski et al. | |
| 2003/0020479 A1 | 1/2003 | Koch et al. | |
| 2006/0039105 A1 | 2/2006 | Smith et al. | |
| 2007/0045019 A1* | 3/2007 | Carter | B60T 7/16 |
| | | | 180/271 |
| 2007/0161904 A1 | 7/2007 | Urbano | |
| 2007/0182367 A1 | 8/2007 | Partovi | |
| 2008/0119730 A1 | 5/2008 | Kim et al. | |
| 2008/0194962 A1* | 8/2008 | Randall | A61B 8/4411 |
| | | | 73/40.7 |
| 2011/0057606 A1 | 3/2011 | Saunamäki | |
| 2012/0016265 A1 | 1/2012 | Peterson et al. | |
| 2014/0188496 A1 | 7/2014 | Ramsey et al. | |
| 2015/0091389 A1* | 4/2015 | Byrne | A61B 5/6891 |
| | | | 307/104 |
| 2016/0023675 A1* | 1/2016 | Hannah | B62B 3/14 |
| | | | 701/2 |
| 2016/0317131 A1 | 11/2016 | Schwartz et al. | |
| 2017/0027541 A1 | 2/2017 | Henderson et al. | |
| 2017/0174093 A1 | 6/2017 | Oettle et al. | |
| 2018/0224853 A1 | 8/2018 | Izhikevich | |
| 2019/0274642 A1 | 9/2019 | MacLaughlin | |
| 2019/0365352 A1* | 12/2019 | Song | A61B 8/565 |
| 2020/0008785 A1 | 1/2020 | Lee et al. | |
| 2020/0171647 A1 | 6/2020 | Theobald | |
| 2020/0389057 A1 | 12/2020 | Hajimiri et al. | |
| 2022/0203007 A1 | 6/2022 | Yuds et al. | |
| 2022/0230714 A1 | 7/2022 | Batman et al. | |
| 2022/0242256 A1 | 8/2022 | Cho et al. | |
| 2022/0249876 A1* | 8/2022 | Krone | A61B 8/4411 |
| 2023/0014078 A1 | 1/2023 | Kayser et al. | |
| 2024/0266074 A1 | 8/2024 | Smurro | |

FOREIGN PATENT DOCUMENTS

| | | | |
|---|---|---|---|
| JP | 2004-261363 A | 9/2004 | |
| JP | 2005-198761 A | 7/2005 | |
| KR | 20180126170 A | 11/2018 | |

OTHER PUBLICATIONS

Final Office Action received for U.S. Appl. No. 17/693,089, mailed on May 1, 2024, 20 pages.
Non-Final Office Action received for U.S. Appl. No. 17/693,089, mailed on Nov. 9, 2023, 18 pages.
Requirement for Restriction/Election received for U.S. Appl. No. 17/693,089, mailed on Sep. 21, 2023, 8 pages.
Non-Final Office Action received for U.S. Appl. No. 17/710,422, mailed on Nov. 7, 2024, 8 pages.
Non-Final Office Action received for U.S. Appl. No. 17/693,089, mailed on Sep. 27, 2024, 23 pages.
Non-Final Office Action received for U.S. Appl. No. 18/426,201, mailed on Sep. 24, 2024, 17 pages.
Requirement for Restriction/Election received for U.S. Appl. No. 18/426,201, mailed on Sep. 10, 2024, 7 pages.
Final Office Action received for U.S. Appl. No. 18/426,201, mailed on Feb. 5, 2025, 17 pages.
Notice of Allowance received for U.S. Appl. No. 17/710,422, mailed on Mar. 13, 2025, 8 pages.
1 Final Office Action received for U.S. Appl. No. 17/693,089, mailed on May 8, 2025, 26 pages.
Notice of Allowance received for U.S. Appl. No. 17/710,422, mailed on Mar. 27, 2025, 2 pages.
Notice of Allowance received for U.S. Appl. No. 17/710,422, mailed on May 21, 2025, 2 pages.
Non-Final Office Action received for U.S. Appl. No. 18/882,336, mailed on Aug. 12, 2025, 23 pages.
Non-Final Office Action received for U.S. Appl. No. 18/426,201, mailed on Jul. 17, 2025, 19 pages.
Final Office Action received for U.S. Appl. No. 18/882,336, mailed on Dec. 9, 2025, 26 pages.
Final Office Action received for U.S. Appl. No. 18/426,201, mailed on Dec. 18, 2025, 23 pages.

* cited by examiner

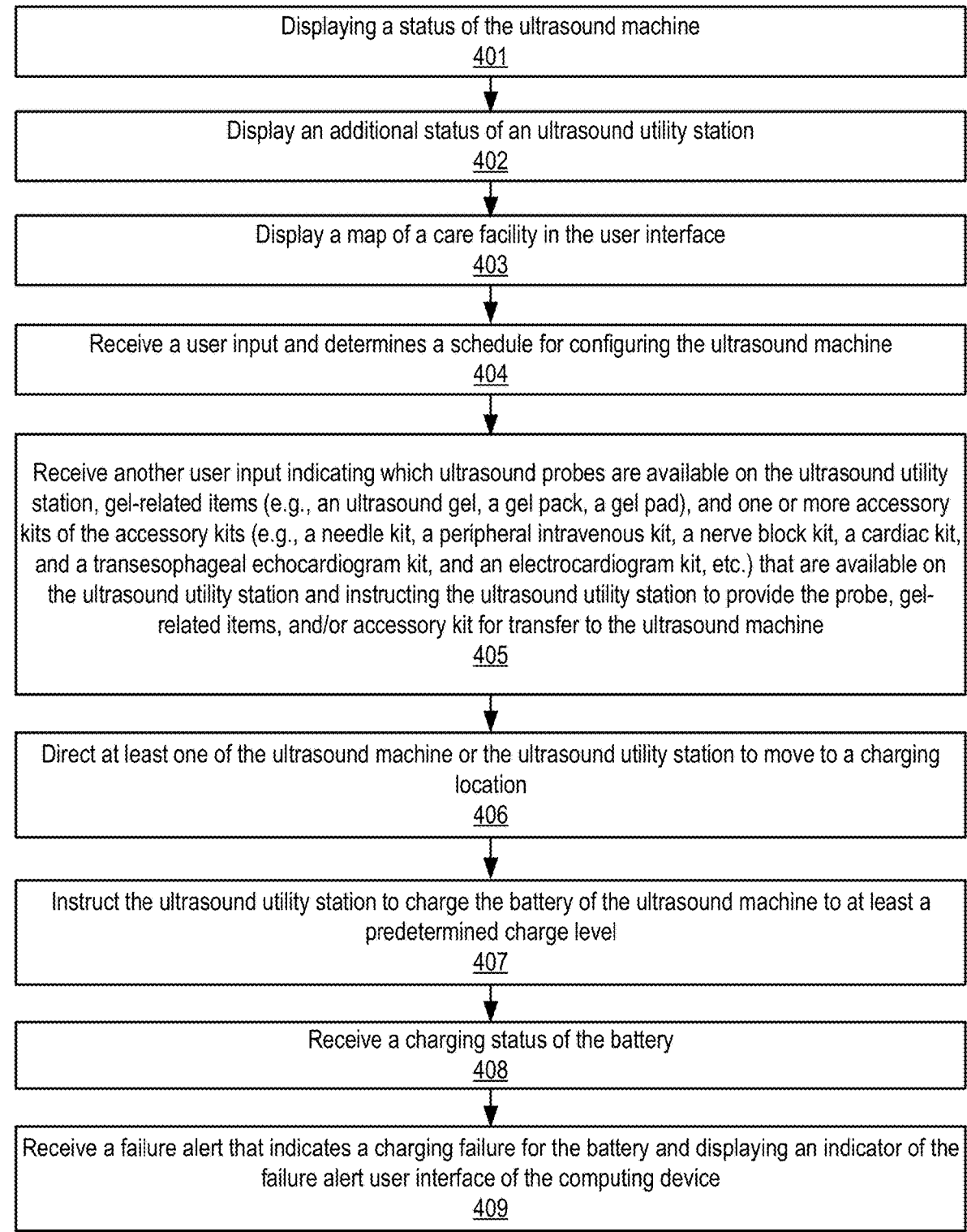

Displaying a status of the ultrasound machine
401

Display an additional status of an ultrasound utility station
402

Display a map of a care facility in the user interface
403

Receive a user input and determines a schedule for configuring the ultrasound machine
404

Receive another user input indicating which ultrasound probes are available on the ultrasound utility station, gel-related items (e.g., an ultrasound gel, a gel pack, a gel pad), and one or more accessory kits of the accessory kits (e.g., a needle kit, a peripheral intravenous kit, a nerve block kit, a cardiac kit, and a transesophageal echocardiogram kit, and an electrocardiogram kit, etc.) that are available on the ultrasound utility station and instructing the ultrasound utility station to provide the probe, gel-related items, and/or accessory kit for transfer to the ultrasound machine
405

Direct at least one of the ultrasound machine or the ultrasound utility station to move to a charging location
406

Instruct the ultrasound utility station to charge the battery of the ultrasound machine to at least a predetermined charge level
407

Receive a charging status of the battery
408

Receive a failure alert that indicates a charging failure for the battery and displaying an indicator of the failure alert user interface of the computing device
409

FIG. 4

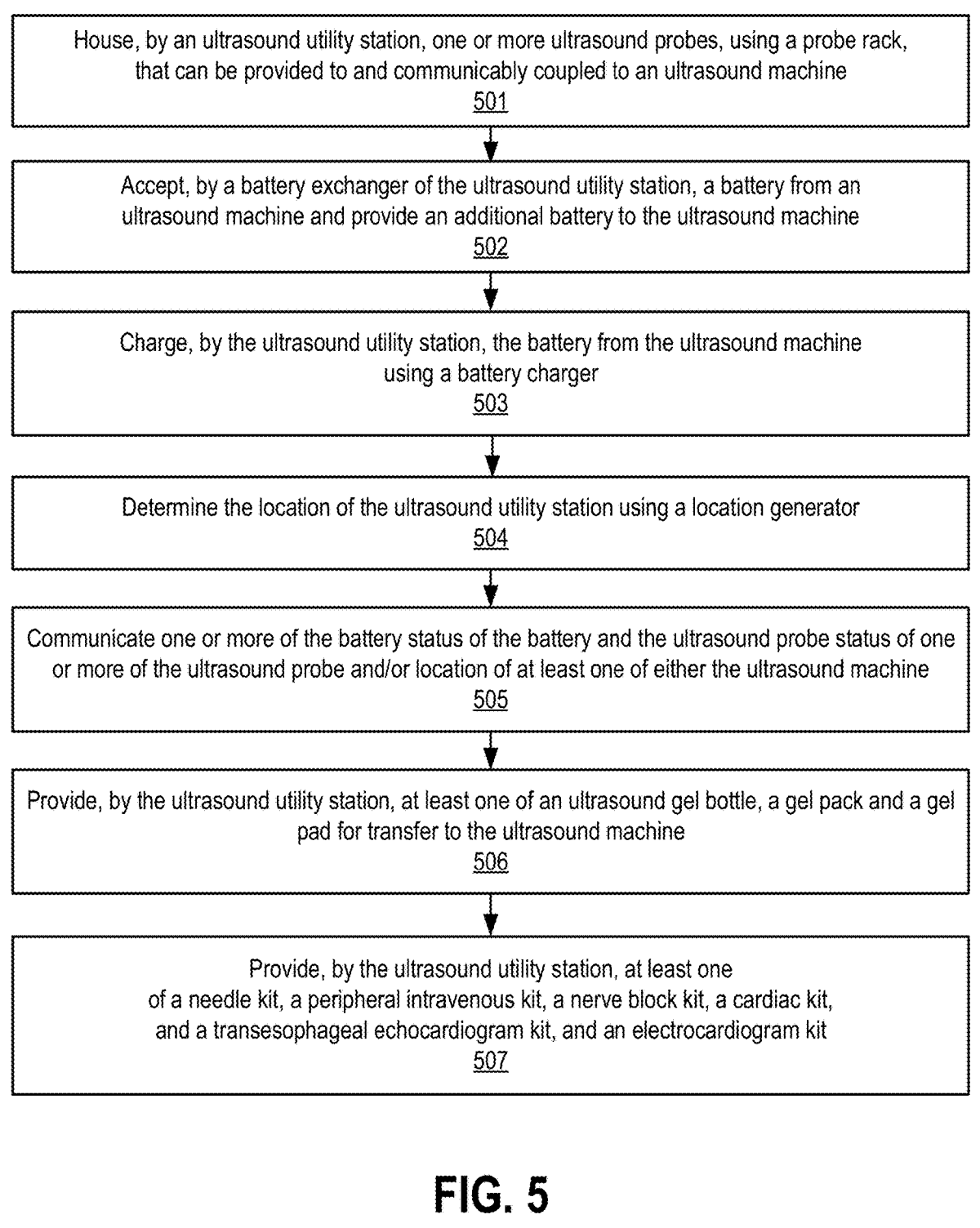

House, by an ultrasound utility station, one or more ultrasound probes, using a probe rack, that can be provided to and communicably coupled to an ultrasound machine
501

Accept, by a battery exchanger of the ultrasound utility station, a battery from an ultrasound machine and provide an additional battery to the ultrasound machine
502

Charge, by the ultrasound utility station, the battery from the ultrasound machine using a battery charger
503

Determine the location of the ultrasound utility station using a location generator
504

Communicate one or more of the battery status of the battery and the ultrasound probe status of one or more of the ultrasound probe and/or location of at least one of either the ultrasound machine
505

Provide, by the ultrasound utility station, at least one of an ultrasound gel bottle, a gel pack and a gel pad for transfer to the ultrasound machine
506

Provide, by the ultrasound utility station, at least one of a needle kit, a peripheral intravenous kit, a nerve block kit, a cardiac kit, and a transesophageal echocardiogram kit, and an electrocardiogram kit
507

FIG. 5

ULTRASOUND UTILITY STATION

This application is a continuation application of co-pending U.S. patent application Ser. No. 17/710,422, filed Mar. 31, 2022, which is a continuation application of U.S. patent application Ser. No. 17/693,089 filed Mar. 11, 2022, and claims priority of all of the above filing dates.

FIELD OF THE INVENTION

The embodiments disclosed herein relate generally to ultrasound imaging; more specifically, the embodiments disclosed herein relate to the use of charging stations with ultrasound machines.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and can provide immediate imaging results without delay, ultrasound systems are often used at the point of care, such as in an emergency room or in a patient's hospital room. To minimize hazards at the point of care locations, ultrasound systems usually operate from battery power, rather than requiring a cable connection to an external power supply (e.g., by being plugged into a 120V wall outlet). Consequently, many care facilities use charging stations for ultrasound machines. The charging stations are usually stationary within the facility and can transfer power from a main power supply, e.g., a 120 V wall outlet, to a battery of an ultrasound machine. Once charged, the ultrasound machine can be detached from the charging station and deployed to the point of care location.

However, charging the batteries of ultrasound machines from a charging station connected to a main power supply is time consuming, and while the ultrasound machine is charging, it is not deployed for use at a point of care location. It is not uncommon for the charging time to exceed several hours, and this charging time is exacerbated by the larger batteries included in many modern ultrasound machines. Hence, an ultrasound machine can spend a significant percentage of time docked at a charging station, rather than being deployed at a point of care location.

Furthermore, when an ultrasound machine is at a charging station, operators usually assume that the ultrasound machine is being properly charged by the charging station. However, just because an ultrasound machine is located at a charging station does not necessarily mean that the ultrasound machine is being properly charged. For example, the power connection between the ultrasound machine and the charging station may be a poor or inadequate connection. In some cases, the mating surfaces can become cracked or worn, due to the weight of the ultrasound machine and its improper handling over time. In another example, an error can occur during charging, such as a software charging error, which can cause the ultrasound machine to stop charging. In still another example, the ultrasound machine can be inadvertently bumped or moved by hospital staff, thus causing a poor or inadequate connection between the ultrasound machine and the charging station. As a result, an operator may retrieve an ultrasound machine from a charging station, only to find that the ultrasound machine is not adequately charged, and therefore cannot be deployed to a point of care location.

Many facilities include multiple charging stations, which can be located at various positions throughout the facility. In this case, a first operator may think that an ultrasound machine is located at a particular charging station and attempt to retrieve the ultrasound machine for use at a patient's room. However, the first operator may find that the ultrasound machine has been moved from the particular charging station, such as by a second operator associated with a different department in the facility who, after use, returns the ultrasound machine to a different charging station. Hence, the first operator may need to spend an amount of time locating the ultrasound machine, thereby causing a delay in care to the patient and a costly waste of time for the operator.

Moreover, ultrasound machines can be used in a variety of different procedures, such as non-invasive procedures (e.g., to image a patient's bladder) and invasive procedures (e.g., to provide guidance for needle or instrument insertion). Hence, ultrasound machines often include accessories that are suitable for one or more types of procedures. For example, an ultrasound machine configured to provide guidance for needle insertion can include a peripheral intravenous (PIV) kit that includes tools specific to PIV, such as a needle guide and a PIV-specific transducer, whereas an ultrasound machine configured for cardiac examinations can include a cardiac kit that includes tools specific for cardiac examinations, such as Electrocardiogram (ECG) leads and a cardiac-specific transducer.

In some cases, an operator may retrieve an ultrasound machine from a charging station to find that the ultrasound machine is improperly configured for the type of examination to be performed by the operator. For instance, the operator may have thought that the ultrasound machine was configured with a PIV kit, only to find that the ultrasound machine at the charging station is configured with a cardiac kit, or lacking any suitable kit. Additionally or alternatively, the accessory kit included in the ultrasound machine being charged by the charging station can include the correct type of kit for the examination type, but the kit may not be suitably cleaned and sterilized. Hence, the operator may need to locate the proper accessory kit suitable to the examination and/or clean the accessory kit, which can cause a delay in patient care.

Hence, conventional charging systems for ultrasound machines can fail to adequately charge an ultrasound machine, or otherwise cause the ultrasound machine to be unsuitable for deployment to a point of care location for an ultrasound examination. Moreover, conventional charging systems for ultrasound machines can cause a significant delay in the ultrasound examination at the point of care location, resulting in a poor patient experience and wasted time for the operator of the ultrasound machine. Thus, conventional charging systems for ultrasound machines may not be acceptable for use in some facilities and for some ultrasound examinations.

SUMMARY

A method and apparatus are disclosed herein for using a charging station with an ultrasound machine. In some embodiments, the method is implemented by a computing device for configuring an ultrasound machine to be ready for use and includes displaying a status of the ultrasound machine. In some embodiments, the status of the ultrasound machine is displayed in a user interface of the computing device. In some embodiments, the status may indicate a location of the ultrasound machine and an amount of charge of a battery of the ultrasound machine. In some embodiments, the method also includes displaying, in the user interface, an additional status of an ultrasound utility station, where the additional status indicates an additional location of the ultrasound utility station and one or more available ultrasound probes on the ultrasound utility station. The method also includes receiving, via the user interface, a first user input indicating a selection of an ultrasound probe of the available ultrasound probes and receiving, via the user interface, a second user input that determines a schedule for said configuring the ultrasound machine. The schedule may indicate a time window and a charging location corresponding to the location, the additional location, or a user-selected location that is different from the location and the additional location. The method also includes instructing the ultrasound utility station to, during the time window and at the charging location, charge the battery of the ultrasound machine and provide the ultrasound probe for transfer to the ultrasound machine.

In some embodiments, the apparatus is an ultrasound utility station to configure an ultrasound machine to be ready for use, where the ultrasound utility station includes: a battery exchanger configured to accept a battery from the ultrasound machine and provide an additional battery for the ultrasound machine; a battery charger configured to charge the battery from the ultrasound machine; a probe rack configured to house ultrasound probes that can be coupled to the ultrasound machine; a location generator configured to determine a location of the ultrasound utility station; and a transceiver configured to communicate one or more of a battery status of the battery, a battery status of the additional battery, an ultrasound probe status of one or more of the ultrasound probes, and the location to at least one of the ultrasound machine and a user device.

In some embodiments, the apparatus is an ultrasound utility station including: a transceiver configured to receive statuses of ultrasound machines, the statuses including locations of the ultrasound machines in a care facility and amounts of charge of batteries of the ultrasound machines, where the transceiver is configured to receive additional statuses of additional batteries, and the additional statuses includes locations of the additional batteries in the care facility and amounts of charge of the additional batteries. The ultrasound utility station also includes a scheduler configured to determine, based on the statuses and the additional statuses, a schedule for providing one or more additional batteries to the ultrasound machines, where the schedule includes an order of the ultrasound machines and times for providing those additional batteries.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 4 illustrates a data flow diagram of one embodiment of a process for configuring an ultrasound machine to be ready for use.

FIG. 5 illustrates a data flow diagram of another embodiment of a process for configuring an ultrasound machine to be ready for use

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Systems, devices, and techniques are described herein for using utility stations to provide power for ultrasound machines. This detailed description is organized as follows: a first section describes communications with the ultrasound machine and charging station; a second section describes electrical requirements and connections; a third section describes mechanical attachment of the ultrasound machine to the charging station; a fourth section describes user authentication; and a fifth section describes accessories of the charging station.

Embodiments of Ultrasound Machines and Charging Stations

Figure 1:
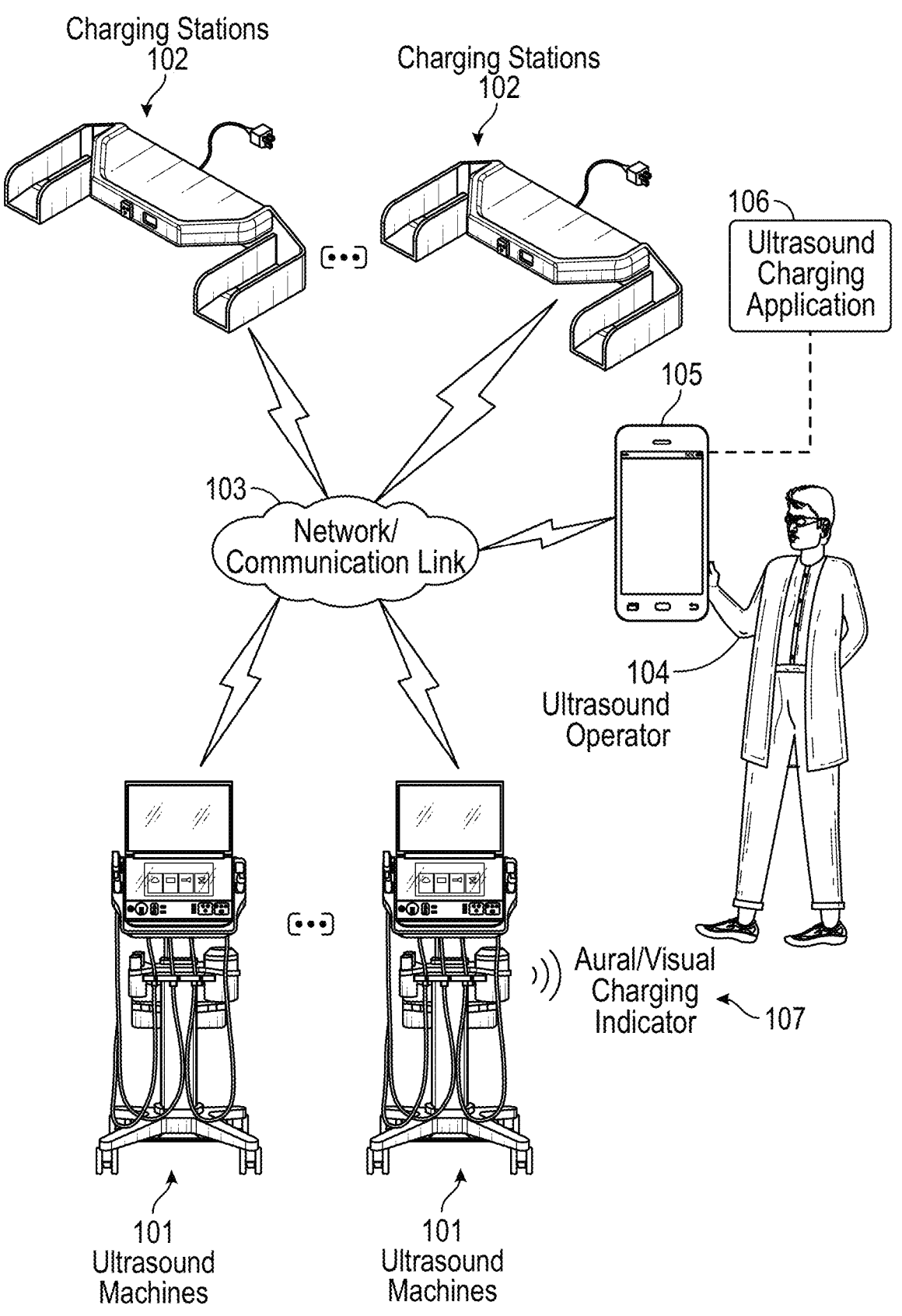
FIG. 1 illustrates a communication environment that includes one or more ultrasound machines and one or more charging stations.

FIG. 1 illustrates a communication environment that includes one or more ultrasound machines 101 and one or more charging stations 102. In some embodiments, charging stations 102 are part of ultrasound utility stations. These ultrasound utility stations can have other features and functionality beyond merely charging capabilities. Similarly, the reference to the term "charging station" herein is not limited to a station that only has charging capabilities, such charging stations may have other features and functionality. Therefore, for purposes herein, the terms "charging station" and "ultrasound utility station" are used interchangeably.

The one or more charging stations 102 are communicatively coupled to each other and to one or more ultrasound machines 101, such as via a network or communication link 103. Network or communication link 103 can include an existing network in a care facility, such as, for example, but not limited to, a Wi-Fi network in a hospital. Additionally or alternatively, network or communication link 103 can include a network dedicated to the ultrasound charging environment. For instance, charging stations 102 and ultrasound machines 101 can include transceivers, such as for near field or short wireless communications, that do not use an existing network in the care facility, e.g., the Wi-Fi network in a hospital.

In some embodiments, the network or communication link includes cooperative communication between units (e.g., ultrasound machines 101 and/or charging stations 102). For example, a first charging station and a second charging station of charging stations 102 can communicate with each other via one or more additional charging stations (or ultrasound machines) when the first and second charging stations are unable to directly communicate with each other. In this example, the one or more additional charging stations (or ultrasound machines) serve as intermediary transceivers between the first and second charging stations. This may occur, for example, when the distance between them is too great.

In some embodiments, charging stations 102 are networked with each other and with ultrasound machines 101 to perform communication to share other information. For example, a charging station receives status information from other charging stations indicating whether they are currently charging an ultrasound machine. In such a case, the charging station can provide information to an ultrasound machine or a user if that particular charging station is not available and direct the user and/or ultrasound machine to another station for charging. Other status information that may be exchanged includes health status information (e.g., an indication that an ultrasound machine or charging station is ready for use, an indication of whether an ultrasound machine or a charging station is currently operating or is not available, etc.), battery status information, an indication of the transducers that are communicably connected to a particular ultrasound machine, and an indication of the last time the ultrasound probes, or portion thereof, underwent a cleaning process.

In another example, charging stations 102 and ultrasound machines 101 may exchange information to enable charging stations 102 to locate ultrasound machines 101 and vice versa to enable the charging of the ultrasound machines to occur. In some embodiments, the information being provided to a charging station from an ultrasound machine (or from another network location) includes an indication of the last charging profile of an ultrasound machine (and its associated battery). This information enables the charging stations to provide a particular or directed charging process (e.g., a charging process designed to extend the battery longevity, etc.).

Note that the information exchanged is not limited to information communicated between ultrasound machines 101 and charging stations 102. In some embodiments, the information is exchanged with one or more parties or locations outside of the immediate environment (e.g., outside of a health care facility). For example, the communication information that is exchanged may be aggregated and provided to a monitoring system that enables the proper maintenance and functionality of the system. For example, such information may be used to trace all components within the system or provide information to the necessary individuals (e.g., sales people) to enable supplies and maintenance to be provided to ensure that all the ultrasound equipment is available for use. For example, such information may track the use of transducers in the ultrasound machine and when one is no longer operational or reaching its end-of-life, a notification can be sent to a sales person or other supplier to enable the supplier to provide new or replacement transducers.

The environment in FIG. 1 includes an ultrasound operator 104, such as a clinician or sonographer, who is trained to operate the ultrasound machines. Ultrasound operator 104 may also operate a computing device 105, such as, for example, a tablet or smartphone. In some embodiments, computing device 105 is issued by the care facility. In some embodiments, computing device 105 includes an ultrasound charging application 106 that allows ultrasound operator 104 to communicate with, and view data about, ultrasound machines 101 and/or charging stations 102. For instance, in some embodiments, ultrasound charging application 105 can allow ultrasound operator 104 to perform asset tracking by locating ultrasound machines 101 and/or charging stations 102 in the care facility. In one example, ultrasound charging application 106 displays a map of the care facility and indicates on the map the locations of the ultrasound machines and charging stations. Additionally or alternatively, the displayed locations can indicate an amount of charge (e.g., time or percentage of remaining battery life) on the ultrasound machines. In some embodiments, these indications are provided via icons or other graphical elements (e.g., colored icons, etc.). For instance, the locations of ultrasound machines 101 can be indicated by circles on the map displayed by ultrasound charging application 106, and the circles can be colored according to the battery and/or charge status of the ultrasound machines, such as, for example, green indicating a charge above a first threshold, red indicating a charge below a second threshold, and black indicating an ultrasound machine is in use by another ultrasound operator.

In some embodiments, ultrasound charging application 106 displays a user interface through which ultrasound operator 104 may access a status window for each ultrasound machine of ultrasound machines 101 and each charging station of charging stations 102. For example, ultrasound operator 104 may touch an icon that indicates a particular ultrasound machine, charging station, or other device in the facility, and responsive to the touch, ultrasound charging application 106 can display the status window for the selected unit (e.g., an ultrasound machine, a charging station, etc.). In some embodiments, ultrasound charging application 106 can display any suitable type of status, and is not limited to status regarding a charging state. For instance, ultrasound charging application 106 can display a cleaning status, a status of transducers included with the ultrasound machine, a status of image memory (e.g., memory used, an amount of memory available, etc.), and the like.

Figure 2:
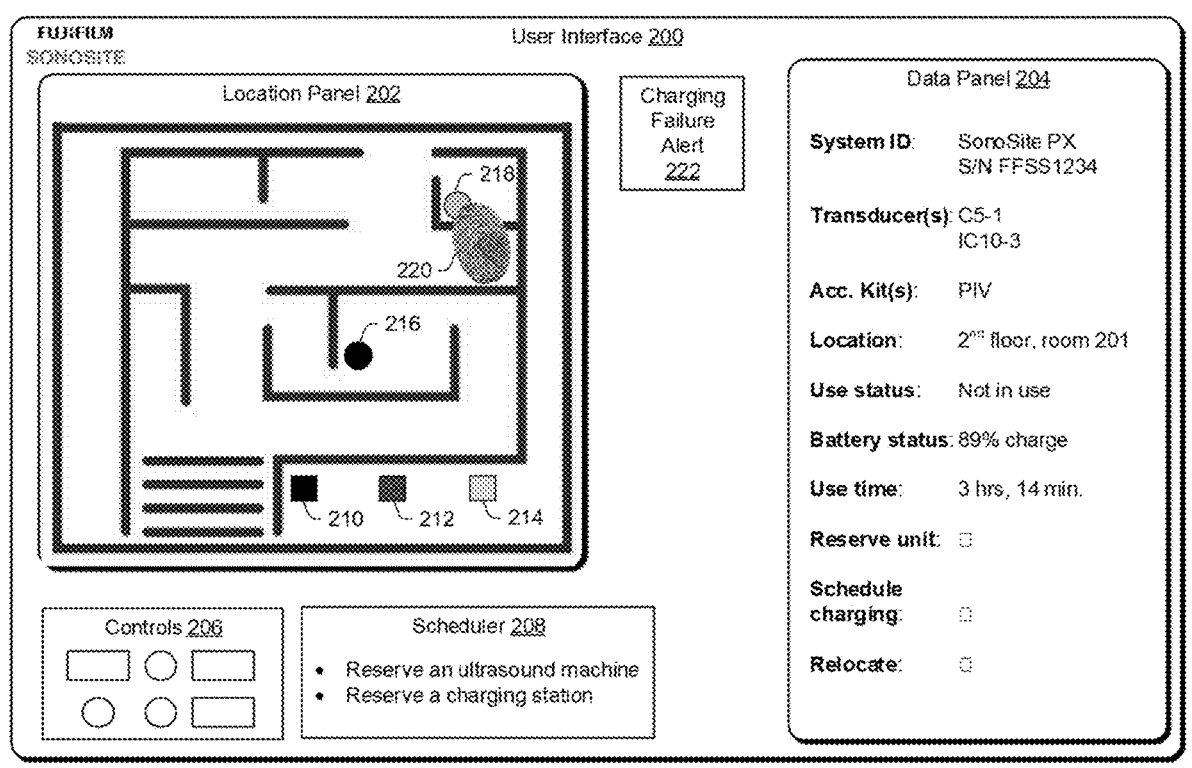
FIG. 2 illustrates an example user interface that can be displayed via an ultrasound charging application.

FIG. 2 illustrates an example user interface 200 that can be displayed via an ultrasound charging application, such as, for example, ultrasound charging application 106 of FIG. 1. In some embodiments, user interface 200 includes location panel 202, data panel 204, controls 206, and scheduler 208. Location panel 202 illustrates a floor plan of a care facility (e.g., a map), and includes icons that indicate the location of ultrasound machines and charging stations in the care facility. For instance, squares 210, 212, and 214 indicate charging stations, and circles 216 and 218 indicate ultrasound machines. In some embodiments, squares 210, 212, and 214 are illustrated with different colors, shadings, or patterns, to indicate any suitable status of the charging stations. For instance, square 210 can be indicated as black to denote that the charging station represented by square 210 is not available, e.g., it is charging an ultrasound machine, off-line, out of service, and the like. Square 212 can be indicated with a hashed pattern to denote that the charging station is currently open and available, but is scheduled to receive an ultrasound machine within a specified time, such as within an hour, or within an amount of time that it would take to charge an ultrasound machine. Square 214 can be indicated with a solid grey to denote that the charging station is currently open and available, and that it is not scheduled for use within a specified amount of time.

Location panel 202 illustrates that two ultrasound machines are located on the floor plan with circles 216 and 218. Circles 216 and 218 are illustrated with different colors, shadings, or patterns to indicate any suitable status of the ultrasound machines. For instance, circle 216 can be indicated as black to denote that the ultrasound machine represented by circle 216 is not available, e.g., it is currently deployed at a point of care location by an ultrasound operator. Circle 218 can be indicated as grey (or green, etc.)

to denote that the ultrasound machine represented by circle 218 is available with an adequate charge. In one example, the color of circle 218 denotes a configuration of the ultrasound machine represented by circle 218, e.g., an accessory kit included with the ultrasound machine, a model of the ultrasound machine, a type of probe included with the ultrasound machine, and the like.

In the example in FIG. 2, a user touches the touch screen that displays user interface 200, and the touch is denoted by touch 220 that selects circle 218. Responsive to the touch 220, user interface 200 can display data panel 204 that displays any suitable data related to the ultrasound machine represented by circle 218. For example, in some embodiments, data panel 204 can display system identification information that identifies a model and serial number of the ultrasound machine (e.g., SonoSite PX with serial no. FFSS1234), a list of transducer probes and accessory kits currently included with the ultrasound machine (e.g., transducers C5-1 and IC10-3, and a PIV accessory kit), a location of the ultrasound machine (e.g., room 201 on the second floor), a use status of the ultrasound machine (e.g., not currently in use), and/or a battery or available power status of the ultrasound machine (e.g., a percentage of battery life remaining, an estimated operation time of the ultrasound machine based on the battery life remaining, etc.).

In some embodiments, data panel 204 also includes options that can be selected to perform an action on the ultrasound machine. For instance, data panel 204 can display an option to reserve the ultrasound machine. When this option is selected, user interface 200 can display in data panel 204 or open another data panel that displays a menu to reserve (e.g., schedule for use) the ultrasound machine (not shown for simplicity). The menu can include a time-table with selectable time frames during which an operator can reserve the ultrasound machine for use.

In some embodiments, data panel 204 also displays an option to schedule charging of an ultrasound machine. When this option is selected, user interface 200 can display in data panel 204 or open another data panel (e.g., a schedule panel, not shown) that displays a menu that can include options to charge the ultrasound machine at a prescribed timeframe. For instance, the menu can include a timetable with select-able time frames, a list of charging stations that can be selected to charge the ultrasound machine, options to relo-cate the ultrasound machine, the charging station, or both to a designated location for charging, options to configure the ultrasound machine with an accessory kit when charging, and the like.

In some embodiments, data panel 204 also displays an option to relocate an ultrasound machine (or a charging station) to a desired location that can be selected on the map of location panel 202. For instance, data panel 204 can enable a user to select an ultrasound machine, touch a location on the map of location panel 202, and cause the ultrasound machine to autonomously move to the indicated location (e.g., to the user). In an example, the operator can schedule a time at which the ultrasound machine should relocate to the indicated location.

In some embodiments, user interface 200 displays infor-mation that may or may not have been specifically requested by an operator. For instance, user interface 200 can indicate that an ultrasound machine's battery is low, that an ultra-sound machine has incurred an error (e.g., the ultrasound machine is stuck and unable to move), that an unauthorized or unauthenticated user has detached an ultrasound machine from a charging station, and the like.

Although the example in FIG. 2 denotes data panel 204 as displaying data regarding a selected ultrasound machine (in this case the ultrasound machine represented by circle 218), data panel 204 can also display information regarding a charging station. For instance, a user can select one of squares 210-214, and data panel 204 can display data regarding the selected charging station.

In some embodiments, user interface 200 also includes controls 206 for controlling an ultrasound machine or charg-ing station, such as controls for gain, depth, presets, drive signals, filters, pulse widths, charging current, charging time, battery configuration, battery selection, etc. Controls 206 also can include any suitable controls for user interface 200, such as zoom, map selection (e.g., select one of multiple floors or one of multiple buildings in the care facility), and the like.

In some embodiments, user interface 200 also includes scheduler 208, which can include any suitable option to schedule or reserve for use an ultrasound machine and/or charging station. For example, responsive to selection of an option in scheduler 208, user interface 200 can display a schedule panel (as described above) to enable an operator to reserve an ultrasound machine and/or charging station dur-ing a specified time frame. In one example, the operator can select which ultrasound machine is charged by which charg-ing station, and a location and time frame for the charging. Hence, an ultrasound operator who may have the weekend off from work can schedule the charging of an ultrasound machine so that it is properly charged and ready for use (e.g., configured with a desired accessory kit) on Monday morning when the operator returns to work.

When an ultrasound machine is in proximity of a charging station and is configured for charging, the charging can fail, such as caused by a poor or inadequate connection, worn or cracked mating surfaces, a software charging error, or an inadvertent bump or movement by hospital staff, as described above. Accordingly, in some embodiments, user interface 200 includes charging failure alert 222 that can indicate to an operator the charging failure. For example, charging failure alert 222 can include one or more icons, lights, alarms, etc. that can cause an audio or video indica-tion denoting the failure. In some embodiments, an operator can select charging failure alert 222, e.g., via a touch, and responsive to the selection, user interface 200 displays a failure panel (not shown for clarity) that displays informa-tion regarding the failure, such as, for example, an identi-fication of the ultrasound machine and charging station, their location, a failure status code (e.g., a code that denotes an excessive temperature, a code that denotes a poor connec-tion, a code that denotes a software assert, and the like).

In some embodiments, when an ultrasound machine is in proximity of a charging station and is configured for charg-ing, the ultrasound machine itself can indicate a status of the charging. For example, a screen of the ultrasound machine can display a first color (e.g., green) to indicate that the ultrasound machine is properly charging. When the ultra-sound machine is not properly charging, the screen can display a second color (e.g., red) to indicate that the ultra-sound machine is not properly charging. By making the entire screen display a single color, the charging status of the ultrasound machine can be easily seen by hospital staff. For example, a casual glance from across a room can confirm the charging status, and requires less effort than physically going to the ultrasound machine and examining a small status indicator, such as an LED. Additionally or alterna-tively, the ultrasound machine and/or charging station can broadcast an audio indicator of charging status, such as "I'm close but not charging, fix me", or "charging okay".

In some embodiments, the ultrasound charging application (e.g., ultrasound charging application 105) and user interface 200 displays different views based on the role of the user. For example, the ultrasound charging application can distinguish between users' roles, or job functions, such as department head, service, sales, and other user roles and/or can determine the usage data of each ultrasound system in the department and provide different views via the user interface for each role. In some embodiments, ultrasound charging application 105 gathers the usage information. Such usage information can be gathered by the ultrasound utility stations and/or ultrasound machines and provided (e.g., sent wirelessly) via network 103 to ultrasound charging application 105. In some embodiments, ultrasound charging application 105 also gathers location information related to the locations of ultrasound machines 101 and/or ultrasound utility stations. This location information can be sent, along with the usage information, to ultrasound charging application 105.

Electrical Requirements and Connections of Embodiments

In some embodiments, the ultrasound machine and the charging station operate in conjunction to transfer power to the ultrasound machine. In one example, the ultrasound machine is moved to a location of the charging station. For instance, the ultrasound machine can include a motion mechanism, such as, for example, an electric motor and wheels, to facilitate autonomous movement. The ultrasound system may include a guidance system that enables the ultrasound machine to direct and guide itself to the location of the charging machine. In one example, the ultrasound machine includes four wheels. In another example, the ultrasound system includes one wheel in its base, and equilibrium is maintained automatically by gyroscopic sensors and computer-controlled motors. By using a single wheel in its base, the size of the footprint of the ultrasound machine can be reduced, compared to a multi-wheeled base. The ultrasound system can include a failsafe mechanism to park the ultrasound machine and/or maintain equilibrium, e.g., in case a battery dies, or in the case of an emergency, such as an earthquake or fire.

Additionally or alternatively, the charging station can be moved to a location of the ultrasound machine for charging. For instance, the charging station can include a motion mechanism, such as an electric motor and wheel(s), to facilitate autonomous movement. The charging station may include a guidance system that enables the charging station to direct and guide itself to the location of the ultrasound machine. Additionally or alternatively, an operator can instruct both the ultrasound machine and the charging station to a desired location for charging. In one example, the desired location includes a dedicated charging room in the care facility. In another example, the location includes a current location of the operator. In one example, the charging station is integrated into a patient's bed, so that the ultrasound machine can be charged while deployed in a patient's room.

The ultrasound machine and the charging station can include any suitable mechanisms for power transfer. In one example, the charging station includes a power cord that can be connected to a main power supply, such as a 120 V, 60 HZ AC power supply. Hence, the charging station can plug into a wall outlet, such as an elevated (with respect to a floor) wall outlet. The charging station can include an AC to DC converter that converts AC power from the main power supply to DC power that can be safely transferred from the charging station to the ultrasound machine.

The ultrasound machine can be electrically coupled to the charging station in any suitable way. In one example, the ultrasound machine and the charging station are electrically coupled via a power cord that can be magnetically affixed to one or both of the ultrasound machine and the charging station. In an example, the power cord is magnetically affixed to the ultrasound machine and mechanically affixed to the charging station. Since the magnetic coupling can be broken more easily (e.g., with less force) than the mechanical coupling, the ultrasound machine can be pulled or removed from the charging station so that the chord remains with the charging station, rather than being dragged by the ultrasound machine when the ultrasound machine is separated from the charging station.

In some embodiments, the charging station includes a charging mat (or plate) that lays horizontally on a surface, such as the floor. The ultrasound machine can be rolled onto the charging mat for charging, and the charging mat can transfer power from the charging station to the ultrasound machine inductively or via RF power transfer. The charging mat can include printed markings or electronic indicators (e.g., LEDs) to indicate an area on the charging mat to park the ultrasound stand for charging. In one example, the charging mat is embedded into the floor of the care facility, e.g., within a 12 in×12 in floor tile. The charging station can connect to the charging mat via a floor connection, and the ultrasound machine can be placed on the floor tile for inductive power transfer. In an example, the charging station projects an image onto the floor tile to indicate where to place the ultrasound machine, such as an illuminated box that includes the words "park here for charging". Additionally or alternatively, the charging station can project an image that matches a footprint of the ultrasound machine to indicate where to place the ultrasound machine for charging. In one example, the charging mat of the charging station is placed on the wall of the care facility, allowing the ultrasound machine to be parked for charging against the wall, thus getting the ultrasound machine out of a busy space (e.g., walkway) and saving floor space.

In some embodiments, a first ultrasound machine can transfer power to a second ultrasound machine, thus eliminating the need to locate a charging station. For instance, the first ultrasound machine can be equipped with circuitry to generate an electromagnetic field from a battery of the first ultrasound machine. When placed proximate to the second ultrasound machine, the electromagnetic field can inductively couple power to the second ultrasound machine, such as via capacitive coupling.

Additionally or alternatively, the care facility can include charging stations embedded into a floor or wall of the care facility. In such a case, as an ultrasound machine is moved in proximity of the wall or floor, charge can be coupled inductively to the ultrasound machine, thereby charging a battery of the ultrasound machine even as the ultrasound machine is moving. In an example, the charging stations are hidden within the floor or wall (e.g., along an entire hallway), so that an operator does not need to know a specific spot for charging the ultrasound machine. For instance, the floor or wall can include an array (e.g., a linear array) of charging stations.

In some embodiments, the ultrasound machine includes a magneto-type charger that builds charge while the ultrasound machine is moved, like a generator for a bicycle light. The magneto-type charger can be coupled to one or more wheels of the ultrasound machine. When the ultrasound machine is moved and the wheels are turned, the magneto-type charger generates charge that can be transferred to a battery on the ultrasound machine.

As stated herein, a charging station can move to a location (e.g., a location of an ultrasound machine) to charge a battery on the ultrasound machine. In one example, a charging station is modular, so that only part of the charging station is mobile and can move to a location for charging. For instance, a first portion of the charging station can disengage from the charging station and autonomously locate and move to an ultrasound machine, while a second portion of the charging station remains stationary and connected to the charging station. In an example, the charging station can release multiple drones (e.g., a swarm of drones) that can travel to an ultrasound machine, and hover around the ultrasound machine to inductively couple charge to the ultrasound machine. When a satisfactory amount of charge has been transferred, the drones can return to the charging station, such as within a docking bay or compartment of the charging station.

The ultrasound machine and charging station can employ any suitable type of batteries. In one example, the ultrasound machine includes a modular battery that can be removed and replaced, such as with a quick disconnect attachment system. Examples of a quick disconnect attachment include magnetic couplings, ¼-turn fittings, push-pull fittings (e.g., a cable fitting that is pushed to engage, then pushed again and pulled to disengage, similar to an air hose fitting), combinations thereof, and the like. The charging station and ultrasound machine can work in conjunction with each other to automatically swap a modular battery in an ultrasound machine. For instance, when one or both of the charging station or the ultrasound machine determines that a battery of the ultrasound machine should be replaced, the ultrasound machine can include a battery exchanger, e.g., a mechanism to remove the battery to be replaced and receive an additional battery. The charging station can include a mechanism to receive the battery to be replaced, and provide the additional battery to the ultrasound machine. The mechanisms in the ultrasound machine and charging stations for battery swap can include magnetic holders, conveyor belts, tracks, robotic arms, etc. to perform the battery swapping.

In some embodiments, the ultrasound machine and/or charging station includes a verification mechanism to guarantee that authorized batteries are used, and to prevent the use of unauthorized batteries. The verification mechanism can include mechanical and/or electrical components. For instance, the ultrasound machine and/or charging station can include an electrical circuit that receives an identification number (e.g., a code, system identification number, password, etc.) from a battery and checks the identification number against a stored list of identification number to allow charging or deployment of the battery. If the identification number matches an entry on the stored list, the battery can be used; if the identification number does not match an entry on the stored list, the ultrasound machine and/or charging station can reject the battery so it cannot be used. In an example, the identification number is encrypted, to prevent unauthorized access. The battery can communicate the identification number to the ultrasound machine and/or charging station in any suitable way, such as via an RF ID transmitter included in the battery.

Additionally or alternatively, the ultrasound machine, charging station, and batteries can use proprietary connectors to prevent use of a generic, or unauthorized, battery. The form factors of the proprietary connectors can prevent the use of unauthorized batteries that lack the form factors.

Additionally or alternatively, the connectors themselves can include electronic means of verification. For instance, one connector can include a receiver verification circuit, and the mating connector can include a transmitter verification circuit that transmits, wirelessly or through contact of the connectors, a verification code that must be authenticated by the receiver verification circuit to use the battery (e.g., use in the ultrasound machine and/or the charging station).

Modern ultrasound machines can include functionality lacking in traditional ultrasound machines, such as the use of additional monitors, additional processor resources to run sophisticated artificial intelligence (AI), machine learning (ML) algorithms, super-resolution imaging algorithms, and the like. These additional resources often have greater power needs, which require larger-capacity batteries.

When using larger-capacity batteries that require a significant amount of time to charge, in some embodiments, the ultrasound machine and charging station of the current disclosure include a two-stage charging system to allow the ultrasound machine to charge while it is deployed at a point of care location, and reduce the amount of time the ultrasound machine is required to be docked at a charging station and be unavailable for deployment. The two-stage charging system can include a fast-charging component and a slow-charging component. The fast-charging component can include circuitry of the ultrasound machine that can quickly accept a charge from the charging station, but may not be suitable to directly charge the battery of, or power, the ultrasound machine. For instance, the fast-charging component can include a bank of capacitors that can quickly receive a charge from the charging station. For example, the bank of capacitors or capacitor grid of super capacitors can be quickly charged in mere seconds or minutes from the charging station. Once the capacitors receive an adequate charge from the charging station, the ultrasound machine can be deployed to a point of care location, and the slow-charging component can be activated. The slow-charging component can slowly (relative to the charge rate of the fast-charging component) transfer charge from the fast-charging component to the battery of the ultrasound machine. In this way, the ultrasound machine does not need to remain at the charging station to continue to charge, but instead can be charged while it is in use, thus reducing the amount of downtime of the ultrasound machine, and thereby increasing its utility for patient care.

In some embodiments, the fast-charging component is a modular component that can be charged at a charging station and stored as ready-for-use by the charging station. Thus, an ultrasound machine can be coupled to the charging station, and the fast-charging component can be immediately transferred to the ultrasound machine (without waiting for the fast-charging component to be charged) and installed on the ultrasound machine, so that the ultrasound machine is immediately available for use. Hence, the two-stage charging system can quickly fill potential to the fast-charging component, then trickle the potential via the slow-charging component, in an analogous manner to filling an automobile's fuel tank quickly, but burning the fuel at a much slower rate.

In some embodiments, the ultrasound machine includes a battery that does not need to be charged, or has a time between charging that is greater than the lifespan of the ultrasound machine. One example of such a battery is a diamond nuclear battery that combines radioactive isotopes from nuclear waste with layers of paneled nano diamonds. Micro-sized single crystal diamonds can move heat away from the radioactive isotope materials quickly enough that the transaction generates electricity. By combining large numbers of these diamond nuclear cells, a battery with sufficient potential to power the ultrasound machine can be included in the ultrasound machine. By making the cells modular, the charging station can determine and quickly replace faulty cells on the diamond nuclear battery of the ultrasound machine, ensuring that the ultrasound machine is charged and ready for deployment.

In some embodiments, a charging system provides charge to the ultrasound machines via the charging stations according to an optimization criterion. For example, since an ultrasound machine does not generally need to be fully charged to be deployed (rather, it needs an amount of battery life to perform its expected functions until its next charge), the "best" charging solution may be to charge the ultrasound machines with a partial charge for an amount of charging time so that there is, on average, always a prescribed number of ultrasound machines available for deployment with a prescribed minimum amount of charge. The charging system can automatically locate ultrasound machines to charging stations, and/or vice versa, according to a cost function that is optimized over the number of charging stations, number of ultrasound operators working over a time window, the number of ultrasound machines, and expected charge time, subject to a constraint that a charged ultrasound machine has at least a prescribed amount of charge (or charges for a prescribed amount of time). The optimization can be constructed akin to a networking optimization problem. In one example, the optimization can take the form of $$N^* = \underset{N}{\operatorname{argmin}} J(N, M, L, T \mid C(M-N) > C_{min})$$

where N denotes the number of ultrasound machines charging at any time, M denotes the total number of ultrasound machines, L denotes the total number of charging stations, T denotes the average time to charge to a minimum charge $C_{min}$, C(x) denotes the charge of an ultrasound machine x, and J is any suitable cost function.

Mechanical Attachment of Embodiments of an Ultrasound Machine to a Charging Station When the ultrasound machine is configured to be charged by the charging station, the ultrasound machine can be mechanically coupled to the charging station in any suitable way. In some embodiments, the ultrasound machine is retained to the charging station by the force of gravity. For instance, the charging station can include a mat or plate (e.g., a floor mat/plate) onto which the ultrasound machine can be wheeled. The mat can include recesses that capture the wheels of the ultrasound machine, and the weight of the ultrasound machine can retain it on the mat, so that the ultrasound machine does not inadvertently move or roll off the mat. For instance, the force of gravity that keeps the ultrasound machine engaged with the recesses in the mat due to the weight of the ultrasound machine is greater than the force needed to remove the ultrasound machine from the mat/plate. Additionally or alternatively, the mat/plate can include a self-locking mechanism that engages the wheels of the ultrasound machine, such as with a clamp or brake that is automatically deployed once the wheels of the ultrasound machine are positioned in the recesses. The mat/plate can include weight sensors (e.g., scales) to determine when the wheels of the ultrasound machine are positioned within the recesses, and deploy the clamps/brakes based on the sensors reading at least a threshold weight. In some embodiments, the mat/plate is self-leveling. For instance, once the wheels of the ultrasound machine are positioned within the recesses of the mat/plate, the mat/plate can move itself, in whole or in part, to level the ultrasound machine and/or level the mat, thus reducing the chance that an ultrasound machine can inadvertently roll off the mat.

In some embodiments, the charging station projects an image onto the mat/plate to indicate to a user where to place the ultrasound machine. For instance, the charging station can project one or more shapes (e.g., four rectangles, one for each wheel) that outline the recesses in the mat onto which the ultrasound machine wheels are to be placed. Additionally or alternatively, the charging station can project an area on the mat, and once the ultrasound machine is placed within the designated area, the ultrasound machine can automatically and without user intervention self-park on the mat. For example, the ultrasound machine can include a camera or other optical sensor coupled to a processor on the ultrasound machine that implements a steering/parking algorithm that engages electric motors on the wheels to park the ultrasound machine at the desired location on the mat.

In some embodiments, the mat includes tracks (or grooves) and the ultrasound machine can be placed at an initial position so that the wheels of the ultrasound machine are within the tracks/grooves of the mat. Once the ultrasound machine is placed at the initial position, the mat can pull the ultrasound machine along the tracks to automatically park the ultrasound machine, e.g., via magnets, cables, tracks, etc.

In some embodiments, once the ultrasound machine is parked, the charging station can automatically deploy an electrical connector that mates with an electrical connector on the ultrasound machine to facilitate charging. Authentication of the ultrasound machine or battery can be done via the electrical connector, as described above, to prevent unauthorized charging. In an example, the charging station charges the ultrasound machine via inductive charge coupling once the ultrasound machine is parked. By sequencing the parking of the ultrasound machine prior to the electrical coupling of the ultrasound machine with the charging station, the charging system prevents hazardous situations in which an unsecured ultrasound machine is charging.

Hence, docking the ultrasound machine with the charging station can be done in one step by the user, e.g., by placing the ultrasound machine at an initial position with respect to the docking station. The user can then walk away and be confident that the ultrasound machine is charging, thus removing the extra steps of (i) manipulating the ultrasound machine in a final position for charging, (ii) manually locking the wheels of the ultrasound machine, and (iii) manually connecting, electrically, the ultrasound machine to the charging station, saving time for the user.

In some embodiments, the ultrasound machine includes a first mating component, the charging station includes a second mating component, and the ultrasound machine is mechanically connected to the charging station by mating the first mating component with the second mating component. For example, the first mating component can include a tapered shaft with a groove machined on the diameter of the shaft, and the charging station can include a port with a spring-loaded ball bearing. When the shaft is inserted into the port, and slid along the port, the ball-bearing can be pushed into the groove of the shaft by the spring, thus acting as a detent mechanism to secure the ultrasound machine to the charging station. For instance, the shaft can be in the horizontal dimension, and the port can be included in a wall of the care facility. To remove the ultrasound machine from the charging station, the ultrasound machine can be pulled away from the charging station to overcome the force of the detent. Additionally or alternatively, the ultrasound machine can be pushed forward, towards the charging station, and a spring in the port of the charging station can assist the removal of the ultrasound machine by helping to move the groove past the ball, thus requiring less force from the user needed to overcome the detent.

In some embodiments, the first and second mating components make up a latch mechanism. For instance, the first mating component can include a rod, and the second mating component can include a latch that locks to the rod to secure the ultrasound machine to the charging station. Additionally or alternatively, the first and second mating components can include a post and a pop-up paddle that engages the post.

In some embodiments, the ultrasound machine includes a handle with a release trigger that must be engaged to remove the ultrasound machine from the charging station. For instance, the release trigger can be coupled to the detent mechanism described above, causing the detent to be released when the trigger is pulled. By integrating the release trigger with the handle, only a single grab motion (e.g., a combined step to pull and unlock) can be needed to disengage the ultrasound machine from the charging station. Additionally or alternatively, the charging station and/or ultrasound machine can include a foot pedal that must be pressed to mechanically engage and/or disengage the ultrasound machine from the charging station.

Additionally or alternatively, the charging station can include a ramp (or runway), onto which the ultrasound machine can be rolled. The ramp can be configured to rotate, or tilt, like a see-saw. When the user stands in a first spot on the ramp, the ramp tilts forward so that the ultrasound machine can be easily moved to a desired position for mechanically locking to the charging station. This desired position can be an initial position, from which the ultrasound machine is automatically moved to a final position suitable for charging, as described above. To remove the ultrasound machine from the charging station, the user can stand in a second spot on the ramp, causing the ramp to tilt backwards. By tilting the ramp backwards, the ultrasound machine can be disengaged mechanically and electrically from the charging station. By using the weight of the user stepping on the ramp, the entire weight of the ultrasound machine does not have to be borne by the user, making it easier and safer to engage and disengage the ultrasound machine from the charging station. Moreover, since the ramp must be tilted backwards to disengage the ultrasound machine from the charging station, the ramp makes it unlikely that the ultrasound machine will accidentally disengage from the charging station, reducing the chances of a charging failure and/or errant ultrasound machine in the middle of the hallway.

In some embodiments, the charging station lifts the ultrasound machine off the floor of the care facility, so that the floor space is kept clear. For example, the charging station can include a lift mechanism to lift the ultrasound machine along a wall, and off the floor. Additionally or alternatively, the charging station can be mounted on a ceiling of the care facility, and lift the ultrasound machine to a mechanical attachment located on the ceiling. The attachment can be recessed into the ceiling, so that the ultrasound machine is lifted to a height that leaves headroom so that a user can walk underneath the ultrasound machine and not hit their head, without ducking.

User Authentication

In some embodiments, the ultrasound machine includes user authentication controls to provide various security functions. For example, in some embodiments, the ultrasound machine can be disengaged, or unlocked, from the charging station by an authorized user, such as a registered ultrasound operator. In some embodiments, the authorized user can carry a key fob that unlocks the ultrasound machine for disengagement when the authorized user is within a prescribed distance from the ultrasound machine and/or charging station, such as ten feet. Additionally or alternatively, the ultrasound machine can include a handle or component that must be touched to unlock the ultrasound machine. The handle or component can include a capacitance sensor that senses the capacitance from the user touch. Additionally or alternatively, the ultrasound machine or charging station can include a scanner for reading a badge or card carried by the authorized user, who can swipe the badge or card to unlock the ultrasound machine from the charging station.

In some embodiments, the ultrasound machine and/or charging station is configured to verify an authorized user without an active, dedicated authentication action by the user, and/or without knowledge by the user of the authentication, and/or without delay to the user caused by the authentication. In some embodiments, these user authentication controls may include a biometric scanner or other biometric sensor to confirm a user's identity. Such a biometric identification system is used to enable the ultrasound machine to be unlocked from the charging station or other location and to be taken by the user for use. In some embodiments, a biometric authentication control is used to identify the user and the ultrasound machine determines if that user is an authorized user. Other biometric controls include a facial recognition algorithm, fingerprint reader on the handle of the ultrasound machine, ear region identifier, eye scanner, combinations thereof, and the like, to authenticate a user.

In some embodiments, when a user is not authenticated, e.g., does not have a required badge or key fob, or fails a biometric authentication algorithm, the ultrasound machine can implement an override mechanism to still allow the user to unlock and disengage an ultrasound machine so that it can be deployed at a point of care location, since a patient's care may critically depend on the ultrasound machine. In this case, the system can require an additional step be performed by the user that would not be required if the user was properly authenticated, such as pressing a button on the ultrasound machine, e.g., a "release now" button. When this additional step is performed and the ultrasound machine is released, the ultrasound machine and/or charging station can generate an alert. The alert can be logged into a data file, emailed to a registered user for the ultrasound machine (e.g., a last-known authorized user of the ultrasound machine), emailed to an equipment administrator, displayed on a user interface of the ultrasound charging application described above, and the like. The alert can include text that describes the event, such as date, time, ultrasound machine identification number, charge status of the ultrasound machine, and the like. Additionally or alternatively, the alert can include an image of the unauthenticated user to whom the ultrasound machine is released. For instance, when the additional step is performed by the user to release the ultrasound machine, the ultrasound machine and/or charging station can capture an image of the user with a camera integrated into the ultrasound machine and/or charging station, and/or with a security camera mounted in the care facility.

Examples of Accessories of for a Charging Station

As discussed above, the charging station can include batteries and other charging system components that can be removed from the charging station and transferred to the ultrasound machine for deployment at a point of care location. In some examples, the charging station can transfer the batteries and charging system components to the ultrasound machine automatically and without user intervention, as described above. Additionally or alternatively, in some embodiments, the charging station can include accessories other than the batteries and charging system components that can be useful for operation of the ultrasound machine.

In some embodiments, the charging station includes a mounting assembly to house cables for the ultrasound machine, such as probe cables, ECG leads, cables for a respiratory sensor, and the like. Additionally or alternatively, the charging station can include ultrasound gel accessories, such as a gel dispenser, gel bottles, gel packs, gel pads that can be affixed to a patient's skin, and the like. In some embodiments, the charging station includes cleaning wipes.

In some embodiments, the charging station includes a mounting assembly to house extra scanheads (e.g., ultrasound probes). The mounting assembly of the charging station can include an area for charging wireless probes that do not require a cable to connect to the ultrasound machine. The area can include electrical charging connectors suitable for charging the batteries included in the wireless probes, so that the wireless probes are charged by the charging station and remain ready for transfer to an ultrasound machine. In some embodiments, the wireless probes are mechanically coupled to the charging connectors, such as, for example, by gravity, magnets, a proprietary connector, combinations thereof, and the like.

In some embodiments, the charging station includes modular kits that can be transferred to an ultrasound machine. The modular kits can be specific for a type of ultrasound examination being performed, and can include a PIV kit, a nerve block kit, a cardiac kit, a transesophageal echocardiogram (TEE) kit, an ECG kit, and the like. The kits can be modular, in the sense that they have, or are housed in, a same (e.g., common or universal) form factor. The ultrasound machine can have a mounting mechanism that is complementary to the form factor of the kits, so that the kits easily mount on the ultrasound machine. For example, if the kits have a male mounting lug, the ultrasound machine can have a complementary female mount that accepts the male mounting lug. The mating can be via a quick connect, quick disconnect mechanism.

Additionally or alternatively, the charging station can include a mechanism for cleaning or disinfecting any of the accessories stored on the charging station. For instance, the charging station can include a pod in which probes or other accessories can be cleaned. The pod can be filled with a gas, ultraviolet light, liquid, or any other suitable cleaning agent to disinfect an accessory. In some embodiments, the pod covers wireless probes while they are charging. Additionally or alternatively, the pod can include a dunk tank filled with a liquid cleaning agent in which probes or other accessories can be placed. The pod may not be intended to replace standard and required cleaning procedures. Rather, the pod reduces risk and builds confidence that the accessories remain clean, such as after a standard sterilization procedure, since the care facility can be libel for infections acquired at the care facility.

By housing the accessories on or in the charging station, rather than on the ultrasound machine, the ultrasound machine is kept uncluttered, making its deployment at a point of care location easier and safer. In an example, any of the accessories stored on or in the charging station can be transferred automatically to an ultrasound probe, such as with an exchanger similar to the battery exchanger described above. In some embodiments, an operator can use the ultrasound charging application installed on a computing device, as described above, to remotely configure the ultrasound machine via the charging station so the ultrasound machine is ready for deployment at a current or future time.

Figure 3:
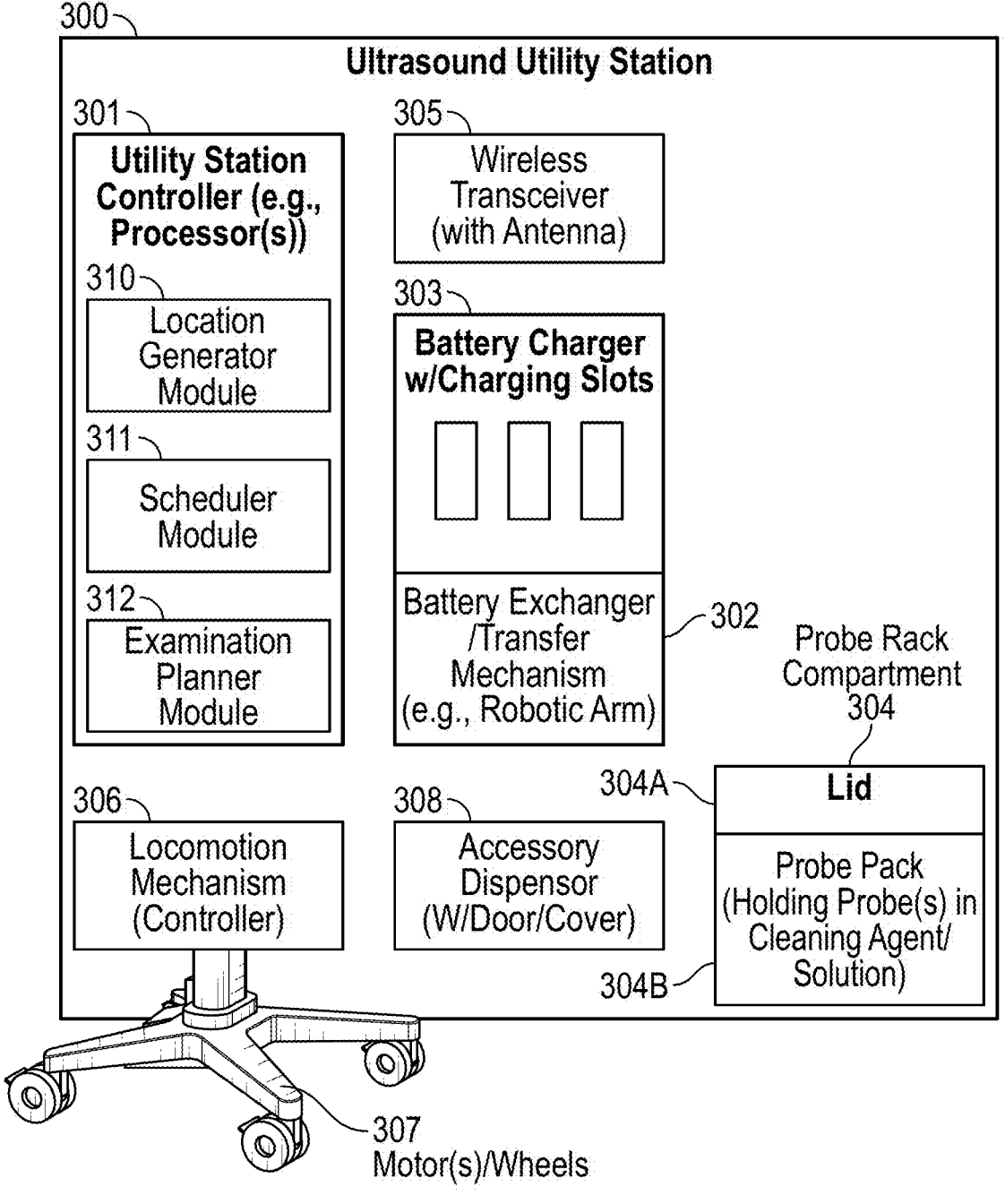
FIG. 3 illustrates some embodiments of an ultrasound utility station along with an ultrasound machine.

In some embodiments, an ultrasound utility station includes one or more of the features described above. The ultrasound utility station is able to configure or otherwise prepare an ultrasound machine to be ready for use. FIG. 3 illustrates some embodiments of an ultrasound utility station along with an ultrasound machine.

Referring to FIG. 3, in some embodiments, the ultrasound utility station 300 includes a transfer mechanism 302 implemented to remove the batteries from the ultrasound machines and transfer the additional batteries to the ultrasound machines. In some embodiments, the transfer mechanism includes a battery exchanger configured to accept a battery from the ultrasound machine and provide an additional battery for the ultrasound machine. In some embodiments, the battery is implemented to provide power to at least one additional ultrasound machine manufactured by a different manufacturer than a manufacturer of the ultrasound machine.

In some embodiments, the ultrasound utility station 300 includes a charger 303 implemented to charge the battery from the ultrasound machine. In some embodiments, the charger charges a battery received from the ultrasound machine and one or more additional batteries that may be used by the ultrasound machine after being transferred to the ultrasound machine via a transfer mechanism.

In some embodiments, the ultrasound utility station 300 includes a probe rack compartment 304 having a lid 304A and probe rack 304B configured to house ultrasound probes that can be coupled to the ultrasound machine. In some embodiments, one or more of the ultrasound probes in the probe rack 304B are implemented to wirelessly communicate to the ultrasound machine and include a rechargeable probe battery. The probe rack 304B may be implemented to charge the rechargeable probe battery of the ultrasound probes. In some embodiments, the probe rack 304B includes a cleaning vessel that contains a cleaning agent to clean the ultrasound probes when the ultrasound probes are housed by the probe rack. Lid 304A can operate to seal probe rack compartment 304.

In some embodiments, the ultrasound utility station 300 includes a location generator module 310 configured to determine a location of the ultrasound utility station. In some embodiments, the location generator module 310 is implemented to determine the location of the battery.

In some embodiments, the ultrasound utility station includes a transceiver 305 configured to communicate one or more of a battery status of the battery, a battery status of the additional battery, an ultrasound probe status of one or more of the ultrasound probes, and the location to at least one of the ultrasound machine and a user device (e.g., the computing device 105 in FIG. 1). In some embodiments, when the location generator module 310 is implemented to determine the location of the battery, the transceiver 305 is implemented to communicate the battery location to one or both of the ultrasound machine and the user device. In some embodiments, the transceiver 305 is implemented to receive, from the ultrasound machine, an indicator of a location of one or more ultrasound machines (e.g., the ultrasound machines in a care facility) and amounts of charge of batteries of the one or more ultrasound machines.

In some embodiments, the ultrasound utility station 300 includes scheduler module 311 configured to determine, based on the statuses and the additional statuses as received by the transceiver 305, a schedule for providing the additional batteries to the ultrasound machines. The scheduler module 311 can include an order of the ultrasound machines and times for providing the additional batteries.

In some embodiments, the ultrasound utility station 300 includes an examination planner module 312 implemented to determine, over a time window based on the amounts of charge of the batteries of the ultrasound machines, planned ultrasound examinations scheduled for the ultrasound machines. In some embodiments, the scheduler module 311 is implemented to determine the schedule based on the planned ultrasound examinations. For example, the order that the ultrasound machines are supplied with batteries can account for the schedule of planned ultrasound examinations.

In some embodiments, location generator module 310, scheduler module 311 and examination planner module 312 are part of a controller 301. In some embodiments, controller 301 controls other operations of ultrasound utility station 300 as well. To that end, controller 301 is communicably coupled to other components of ultrasound utility station 300, including but not limited to, battery exchanger/transfer mechanism 302, battery charger 303, probe rack compartment 304, wireless transceiver 305, location mechanism 306 and accessory dispenser 308. In some embodiments, controller 301 comprises hardware (e.g., processor(s), circuitry, dedicated logic, etc.), software, firmware (e.g., software programmed into a read-only memory), or combinations thereof.

In some embodiments, the ultrasound utility station 300 includes a locomotion mechanism (controller) 306 implemented to move the ultrasound utility station to the locations of the ultrasound machines and the locations of the additional batteries. For example, the location mechanism 306 can include a motor (307) that moves wheels (307) on the ultrasound utility station 300 to enable the ultrasound utility station 300 to move to different locations, including locations of ultrasound machines that need the ultrasound utility station 300 to configure them to be ready for use (e.g., charge their battery, exchange batteries, provide supplies (e.g., gels, kits, etc.), other perform other operations as described herein. These locations may be locations in a care facility.

In some embodiments, the ultrasound utility station 300 includes an ultrasound accessory dispenser 308 implemented to provide, for transfer to the ultrasound machine, at least one of a needle kit, a peripheral intravenous kit, a nerve block kit, a cardiac kit, a transesophageal echocardiogram kit, and an electrocardiogram kit. In some embodiments, the needle kit, the peripheral intravenous kit, the nerve block kit, the cardiac kit, the transesophageal echocardiogram kit, and the electrocardiogram kit have a common mounting form, and the ultrasound machine includes a mount configured to accept the common mounting form. In some embodiments, the ultrasound accessory dispenser 308 includes a gel dispenser implemented to provide, for transfer to the ultrasound machine, at least one of ultrasound gel bottle, a gel pack, and a gel pad. In some embodiments, the ultrasound accessory dispenser 308 includes a door/cover that may be removed to gain access to the accessories.

Note that alternatively the ultrasound utility station 300 may include more or less features than those described above.

Self-Mapping Embodiments

Conventional ultrasound systems and asset tracking systems can result in wasted effort to locate the ultrasound systems within a care facility, resulting in less than optimum patient care. Accordingly, systems, devices, and techniques are described herein for generating care facility maps with ultrasound systems. The ultrasound system can include an ultrasound machine that generates and updates a map of a care facility and can autonomously move to a location on the map.

An ultrasound system can include an ultrasound machine, an ultrasound utility station, one or more displays, a scanner (e.g., probe), etc. In the following, embodiments are generally described with respect to the ultrasound machine. However, any suitable component of the ultrasound system can employ the devices and methods described herein and can work alone or in combination to generate a map of a care facility and the data to generate the map. For example, in some embodiments, an ultrasound utility station generates a map of a care facility and the data to generate the map, such as by using sensors of the ultrasound utility station to generate the data. The ultrasound utility station can share the data and the map with an ultrasound machine and/or another ultrasound utility station.

In one example, an ultrasound machine (and/or, as previously mentioned, an ultrasound utility station) includes one or more sensors. One example sensor includes an inertial measurement unit (IMU) that can measure one or more of force, acceleration, angular rate, and magnetic field. For instance, an IMU can include a combination of accelerometers, gyroscopes, and magnetometers. The data sensed with the IMU can be combined with a known location, such as an initial starting point of the ultrasound machine, to determine a distance traveled and a current location of the ultrasound machine.

Additionally or alternatively, the one or more sensors can include a transceiver configured to sense a property of a communication link in the care facility. For instance, the care facility can include access points, such as, for example, Wi-Fi and/or Bluetooth access points, and the transceiver can connect to the access points. The transceiver can determine any suitable property of the communication with an access point and use the property as data to generate a map of the care facility. For example, the transceiver can determine a signal strength of the communication with an access point. Additionally or alternatively, the transceiver can determine a round trip delay of communications with an access point. As an example, the transceiver can send a ping request to an access point, which in turn sends a ping (e.g., a known data packet, a time stamp, a training signal, or combinations thereof) to the transceiver. The transceiver can determine the round-trip delay as the time from sending the ping request to receiving the ping from the access point. One example of a transceiver is a GPS transceiver configured to determine coordinate positions of the ultrasound machine and/or ultrasound utility station in a global positioning coordinate space.

In an example, the one or more sensors include at least one camera configured to capture images in the care facility. The ultrasound machine and/or ultrasound utility station can use the images as data to generate a map of the care facility. An example of a camera used by the ultrasound machine and/or ultrasound utility station includes a time-of-flight (ToF) camera that not only captures an image, but also determines at least one distance from the ToF camera to an object in the image. For instance, the ToF camera can use ToF techniques to resolve distances between the camera and an object for each point of the image (e.g., each pixel in the image), by measuring the round-trip time of an artificial light signal, such as generated by a laser or an LED. Hence, the ultrasound machine and/or ultrasound utility station can use the images as well as the distances recorded by the ToF camera as data to generate a map of the care facility.

Additionally or alternatively, the one or more sensors can include a reader configured to recognize patterns and visual cues. One example of a reader is a quick response (QR) reader configured to read QR codes that can be placed at various locations within the care facility, such as on a wall of a hallway, at intersections of hallways, on the doors of rooms, at the entrance to departments, etc. The QR code can designate any suitable information, such as a department name, function, level of access required for entry, etc. Additionally or alternatively, a reader can include a bar code reader (e.g., for reading one-dimension or two-dimension bar codes), an optical character reader, a glyph reader, an animation reader, combinations thereof, and the like. For instance, similar to placing QR codes at various locations, the care facility can include bar codes, characters, glyphs, symbols, animations, and the like at various locations to convey any suitable information, as previously discussed with respect to QR codes.

In an example, the one or more sensors include a wheel sensor configured to track a direction and an amount of movement of a wheel on an ultrasound machine and/or an ultrasound utility station. Hence, the ultrasound system can determine a distance and a direction that the ultrasound machine and/or an ultrasound utility station is moved based on the data generated by the wheel sensor.

Additionally or alternatively, an ultrasound scanner (e.g., probe) can itself be used as a sensor of the ultrasound system to generate data that is used to generate a map of the care facility. For example, the care facility can include markers at various locations, such as hidden within walls of the care facility along a hallway, embedded within a floor, inside or attached to a handrail, etc. Similar to the QR codes previously discussed, the markers can be data bearing, and the ultrasound machine can enable the ultrasound scanner to read the data contained within the marker, as well as a distance from the ultrasound machine to the marker. The data and the distance are examples of sensed data that can be used by the ultrasound system to generate a map of the care facility.

In one example, an ultrasound machine is connected to an ultrasound utility station, such as to charge a battery of the ultrasound. The time and location of the charging can be included as sensed data used to generate a map of the care facility, as the location of the ultrasound utility station may be known.

The ultrasound system can use the sensed data generated by the sensors (e.g., on an ultrasound machine and/or an ultrasound utility station) to generate a map of the care facility. The map can take any suitable form. For instance, the ultrasound system can collect the sensed data into a signature that the ultrasound system associates with a location within the care facility. One example of a signature is a feature vector that stores the sensed data from the sensors and/or data derived from the sensed data (e.g., data generated by a neural network that processes the sensed data). The ultrasound machine and/or ultrasound utility station can build feature vectors on-the-fly as the ultrasound machine and/or ultrasound utility station move within the care facility, and associate a feature vector with a determined location in the care facility. Hence, the ultrasound machine and/or ultrasound utility station can store a database of feature vectors and continuously update them as new data is generated by the sensors.

An example of a feature vector is:

$$\vec{f} = [f_1 \cdots f_m f_{m+1} \cdots f_n f_{n+1} \cdots f_p f_{p+1} \cdots ]$$

for integers m, n, and p. In this example, data from a first sensor can be stored in elements $f_1 \cdots f_m$ of the feature vector $\vec{f}$. For example, these elements can store data from a scanner, such as information read from a QR code, a distance to the QR code from the sensor, etc. Data from another sensor can be stored in elements $f_{m+1} \cdots f_n$ of the feature vector $\vec{f}$. For example, these elements can store data from a camera, such as a distance from a ToF camera to a sign imaged by the ToF camera, language contained on the sign that is determined by a character reader (e.g., a model trained to extract text from an image), and data generated from the image by a neural network. For instance, the ultrasound machine and/or ultrasound utility station can include a neural network configured to generate a feature list from an image, such as a convolutional neural network that includes an encoder having progressively down-sampled convolutional layers the extract low-level details of the image and arrange them into the feature list. This feature list generated by the neural network can be included in elements $f_{m+1} \cdots f_n$ of the feature vector $\vec{f}$. Data from still another sensor can be stored in elements $f_{n+1} \cdots f_p$ of the feature vector $\vec{f}$, and the like for other elements of the feature vector $\vec{f}$ and other sensors. Note that as new sensor data becomes available, the ultrasound machine and/or ultrasound utility station can add this data to an existing feature vector and/or create a new feature vector for a new location. If a feature vector does not have elements designated for the sensor data, the ultrasound system can add these elements to the feature vector. For example, if sensor data from a communication link is available (such as round-trip delay and signal strength) but is not included in a feature vector, a section of the feature vector can be added to include this newly available sensed data.

In one example, the signature (e.g., the feature vector) generated by the ultrasound system is initialized with user assistance. For example, a user can move the ultrasound machine and/or ultrasound utility station from an initial location to an additional location and enter these locations into a user interface of the ultrasound machine and/or ultrasound utility station, which can generate feature vectors from sensed data at these locations. The locations can be relative (to one another) and/or absolute (e.g., based on a GPS coordinate system). The distance from the initial location to the additional location can be known (e.g., 100 feet). For instance, the initial location and the additional location can correspond to markers on the floor of a hallway that are separated by the known distance. By entering the locations and the distances between them into the ultrasound system, the user can initialize the feature vectors for these locations that are generated by the ultrasound machine and/or ultrasound utility station by associating these feature vectors with known locations/coordinates. The user can repeat this procedure for any suitable number of known locations, to increase the accuracy and learning speed of the signature generation.

Additionally or alternatively, the ultrasound machine and/or ultrasound utility station can query a user to enter a location. For instance, the ultrasound machine and/or ultrasound utility station can request "Please tell me where I am" via a user interface, and a user can enter a location, such as a description of a department, a room number, a floor number, etc. The ultrasound system can use this user-supplied data to associate a feature vector with a location within the care facility and build a map of the care facility.

Alternatively, the ultrasound system can learn the signatures at locations within the care facility blindly, e.g., without explicit user input. For instance, the ultrasound system can establish a first location from a GPS receiver on the ultrasound system, and the distance to a second location from sensor data (e.g., a wheel sensor or range finder on the ultrasound system). The ultrasound system can generate feature vectors at these and other locations as the ultrasound machine and/or ultrasound utility station is moved within the care facility.

Based on one or more of the signatures (e.g., feature vectors) generated by the ultrasound system, the ultrasound system can determine a current location of a component of the ultrasound system (e.g., an ultrasound machine and/or ultrasound utility station). In one example, the ultrasound system uses a simultaneous localization and mapping (SLAM) algorithm, based on computational geometry and computer vision, to determine a location from one or more signatures (e.g., feature vectors) generated by the ultrasound system. A SLAM algorithm can construct and/or update a map of the care facility while simultaneously tracking the location of the ultrasound machine and/or ultrasound utility station within it. The SLAM algorithm can include any suitable model, filter, and/or algorithm to generate and update the map, including a particle filter, extended Kalman filter, covariance intersection, and GraphSLAM.

Additionally or alternatively, the ultrasound system can determine a current location of a component of the ultrasound system (e.g., an ultrasound machine and/or ultrasound utility station) using a database of feature vectors, such as feature vectors that have been previously generated by an ultrasound system and associated with a known location in the care facility. For example, the ultrasound system can store or access a database of feature vectors for the care facility that each correspond to a different location within the care facility. The ultrasound system can compare the feature vector generated for a current location with the feature vectors in the database, and based on the comparison, determine the current location (e.g., coordinates of the location). The comparison can include any suitable comparison method, such as finding a nearest feature vector to the feature vector generated for the current location, where "nearest" can correspond to any suitable cost function, such as an $\ell_1$ or $\ell_2$ norm of the difference between the feature vectors. Hence, by matching the feature vector generated for the current location to a feature vector in the database, the ultrasound system can determine where in the care facility the current location corresponds.

Additionally or alternatively, the ultrasound system can include one or more neural networks trained to generate a map of the care facility based on one or more signatures (e.g., feature vectors) generated by the ultrasound system. For instance, since different feature vectors can correspond to different locations within the care facility, a neural network can generate a first part of the map from a first set of the feature vectors and a second part of the map from a second set of the feature vectors, and combine the first part and second part to generate the map. As an example, suppose a first set of 128 feature vectors are generated within an East side of the care facility, and a second set of 128 feature vectors are generated within a West side of the care facility. The neural network can process the first 128 vectors to generate a right side of an image, and the second 128 vectors to generate a left side of the image. The ultrasound system can then combine the right side and the left side of the images into a single image (e.g., map or floor plan) of the care facility. The floor plan displayed in the location panel 202 of FIG. 2 is an example of a map generated by the ultrasound system using one or more neural networks and feature vectors generated based on sensor data.

The neural network can generate the map based on any suitable groupings of the feature vectors. In one example, feature vectors are processed by the neural network sequentially (e.g., one at a time) in an order that corresponds to movement of the ultrasound machine and/or ultrasound utility station. For example, suppose the ultrasound machine and/or ultrasound utility station moves in one direction from location A, to location B, and then to location C, and generates a feature vector for each of these locations. The neural network can be configured to process the feature vector for location A, followed by the feature vector for location B, and followed by the feature vector for location C. Additionally or alternatively, the neural network can be configured to process blocks of feature vectors. For instance, feature vectors that correspond to a given area can be grouped, such as by concatenating the feature vectors, and processed by the neural network. A second group of feature vectors corresponding to a different area can then be grouped and processed by the neural network. By grouping feature vectors for different areas that cover the floor plan of the care facility, the neural network can process the different groups of feature vectors and generate a composite map of the care facility.

In one example, different components of an ultrasound system and/or different ultrasound systems can share signatures (e.g., feature vectors) with each other, such as over a communication network within the care facility. Hence, an ultrasound machine can share feature vectors it generates with an ultrasound utility station, and the ultrasound utility station can share feature vectors it generates with the ultrasound machine. Hence, the ultrasound machine and/or ultrasound utility station can update its feature vectors with feature vectors from another device. Further, the ultrasound system can generate a map of the care facility based on feature vectors generated from different devices included within the ultrasound system and/or another ultrasound system.

In an example, the ultrasound system records a time with each feature vector. Hence, the map generated by the ultrasound system can include a time component, so that the ultrasound machine and/or ultrasound utility station can be moved to a given location at a given time. For example, based on the time component of the map, the ultrasound system can determine that the ultrasound machine has been used at 2:30 PM on Thursdays for the last 2 months in an orthopedic department. Hence, the ultrasound machine can determine to autonomously move to the orthopedic department at the next occurrence of Thursday, 2:30 PM. In an example, the ultrasound machine confirms that it is not scheduled for use at the give time (e.g., Thursday, 2:30 PM) or within a time window of the given time prior to autonomously moving to the location associated, via the map, with the given time. Additionally or alternatively, the ultrasound system can include or have access to a worklist. By using the map, the ultrasound system can configure itself based on the worklist (such as with an appropriate accessory or kit) and move itself to a location based on the map to fulfill the worklist.

An example method of generating a map of a care facility can be performed by any suitable computing device, such as one or more ultrasound utility stations, one or more ultrasound machines, and combinations thereof. A method implemented by a computing device to generate a map of a care facility can include receiving, from one or more sensors coupled to the computing device, sensor data corresponding to locations inside the care facility, and determining, for the locations, features of the care facility based on the sensor data. The method can include generating, based on the features, a map of the care facility that includes the locations.

In one example, a computing device implementing the method includes an ultrasound machine, and the sensor data is received as the ultrasound machine is moved to the locations. Additionally or alternatively, the computing device can include an ultrasound utility station configured to charge an ultrasound machine.

In an example, the one or more sensors include a camera, and the sensor data includes an image generated by the camera. Determining the features can include generating, with a neural network implemented at least partially in hardware of the computing device, a feature list based on the image. The features can include feature vectors corresponding to the locations, and generating the map can include generating, with a neural network implemented at least partially in hardware of the computing device, an image based on the feature vectors. In an example, the features include a timestamp indicating a time that the sensor data is generated.

In an example, the method includes communicating the image to an asset tracking application implemented on an additional computing device. In an embodiment, generating the map can include implementing a simultaneous localization and mapping (SLAM) algorithm. Additionally or alternatively, the method can include generating, at a current location of the computing device in the care facility, a current feature vector based on the sensor data corresponding to the current location, and determining the current location on the map based on the current feature vector. Determining the current location can include comparing the current feature vector to a database of feature vectors corresponding to known locations inside the care facility.

In one example, the one or more sensors include a quick response (QR) reader configured to read a QR code displayed in the care facility, and the sensor data includes data read by the QR reader from the QR code. Additionally or alternatively, the care facility can include a first transceiver in communication with a second transceiver of the computing device, and the sensor data can include at least one of a signal strength of the communication and a round trip delay of the communication.

In an example, the method includes receiving a user input indicative of at least one of the locations. The method can include broadcasting an audio request or displaying a visual request to receive the user input. For instance, an ultrasound utility station can broadcast a request for a user to input the current location, such as a room number.

In one example, the one or more sensors include a time-of-flight (ToF) camera configured to generate an image and at least one distance from the ToF camera to an object in the image, and the sensor data includes the image and the at least one distance. Additionally or alternatively, the one or more sensors can include a camera configured to generate an image of a sign displayed in the care facility, and the computing device can include a character reader configured to extract text displayed by the sign. The features can include the text. In an example, the features include a distance from the camera to the sign and an angle in a coordinate system between the camera and the sign.

In one example, the one or more sensors include a camera configured to generate an image of a symbol displayed in the care facility, and the computing device includes a classifier configured to determine a classification of the symbol. The features can include the classification. In an example, the classification includes at least one of a hazardous material, a biohazard material, an X-ray, a nurse station, a patient room, an emergency department, and a pharmacy.

In an embodiment, the one or more sensors include an ultrasound probe configured to generate an ultrasound image of an object in the care facility, and the features include a distance from the ultrasound probe to the object. Additionally or alternatively, the one or more sensors can be configured to determine distances between the locations, and the features include positions based on the distances.

In one example, the method includes receiving, from an additional computing device, additional features for the locations, wherein generating the map is based on the additional features. The method can include sharing the features with the additional computing device. Additionally or alternatively, the method can include receiving, from an additional computing device, additional features for additional locations inside the care facility, wherein generating the map can be based on the additional features, and the map can include the additional locations.

Exemplary Flow Diagrams

FIG. 4 illustrates a data flow diagram of one embodiment of a process for configuring an ultrasound machine to be ready for use. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound utility station or a user device (e.g., computing device 105 in FIG. 1).

Referring to FIG. 4, the process begins by displaying a status of the ultrasound machine (processing block 401). In one embodiment, the status is displayed in the user interface of the computing device. In one embodiment, the status indicates a location of the ultrasound machine and an amount to charge of a battery of the ultrasound machine.

Processing logic also displays an additional status of an ultrasound utility station (processing block 402). In some embodiments, the display of the additional status is in the user interface of the computing device, such as the user interface 200 in FIG. 2. In some embodiments, the additional status indicates an additional location of the ultrasound utility station and the available ultrasound probes on that ultrasound utility station. In some embodiments, the additional status indicates that one or more available accessory kits are available on the ultrasound utility station. In some embodiments, the additional status indicates the cleanliness (e.g., clean/not clean, levels of the cleanliness, etc.) of the ultrasound machine probes.

In some embodiments, the process also includes displaying a map of a care facility in the user interface (processing block 403). In some embodiments, the status of the ultrasound machine includes indicating the location of the ultrasound machine on the map and displaying the additional status of the ultrasound utility station includes indicating the additional location of the ultrasound utility station on the map.

In some embodiments, processing block receives a user input and determines a schedule for configuring the ultrasound machine (processing block 404). In some embodiments, the schedule indicates a time window and a charging location corresponding to the location of the ultrasound utility station, the location of the ultrasound machine or a user-selected location that is different from the location of the ultrasound machine and the location of the ultrasound utility station.

In some embodiments, the process can include receiving another user input indicating a selection of one or more of an ultrasound probe of available ultrasound probes on the ultrasound utility station, gel-related items (e.g., an ultrasound gel bottle, a gel pack, a gel pad), and one or more accessory kits of the accessory kits (e.g., a needle kit, a peripheral intravenous kit, a nerve block kit, a cardiac kit, and a transesophageal echocardiogram kit, and an electrocardiogram kit, etc.) that are available on the ultrasound utility station. The process can also include instructing the ultrasound utility station to provide the probe, gel-related items, and/or accessory kit for transfer to the ultrasound machine (processing block 405). In some embodiments, the ultrasound utility station is instructed to provide these items when the ultrasound machine is at the charging location. In some embodiments, this providing occurs during a time window in which the ultrasound machine is scheduled for configuration.

In some embodiments, processing logic directs at least one of the ultrasound machine or the ultrasound utility station to move to a charging location (processing block 406) and instructs the ultrasound utility station to charge the battery of the ultrasound machine to at least a predetermined charge level (processing block 407). The charge level may be the same as the charge level specified to meet the charge necessary to perform an examination. In some embodiments, the process may also include processing logic receiving a user input indicating a charge level of the battery and instructing the ultrasound utility station to charge the battery to at least a predetermined charge level.

In some embodiments, the process includes receiving a charging status of the battery (processing block 408). In some embodiments, the charging status indicates one or more of a charging level with a battery and a time remaining to fully charge the battery. The charging status of the battery may be received from the ultrasound utility station. In other embodiments, the charging status of the battery may be received from the ultrasound machine. In some embodiments, the charging status of the battery is received during the time window during which the ultrasound machine is scheduled to be configured.

In some embodiments, the process also includes processing logic receiving a failure alert that indicates a charging failure for the battery and displaying an indicator of the failure alert user interface of the computing device (processing block 409). In some embodiments, the failure alert is received from an ultrasound utility station and during a time window that the ultrasound machine is scheduled to be configured.

Note that in alternative embodiments, the process of FIG. 4 may include a subset of the operations shown therein and described above or other operations in addition to one or more of the operations set forth in FIG. 4. For example, in some alternative embodiments, the process includes only displaying a status of the ultrasound machine that indicates a location of the ultrasound machine and an amount of charge of a battery of the ultrasound machine, displaying an additional status of an ultrasound utility station that indicates an additional location of the ultrasound utility station and available ultrasound probes on the ultrasound utility station;

receiving a selection of an ultrasound probe of the available ultrasound probes and a user input that determines a schedule for configuring the ultrasound machine; and instructing the ultrasound utility station to charge the battery of the ultrasound machine and provide the ultrasound probe for transfer to the ultrasound machine.

FIG. 5 illustrates a data flow diagram of a process for configuring an ultrasound machine to be ready for use. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound utility station.

Referring to FIG. 5, the process begins by having an ultrasound utility station housing ultrasound probes, using a probe rack, that can be provided to and communicably coupled (via wired or wireless communication) to an ultrasound machine (501). In some embodiments, one or more of the ultrasound probes are implemented to wirelessly communicate to the ultrasound machine and include a rechargeable probe battery. In some embodiments, the probe rack is implemented to charge the rechargeable probe battery while the probe is in the probe rack. In some embodiments, the probe rack includes a cleaning vessel that contains a cleaning agent to clean the ultrasound probes while the ultrasound probes are housed by the probe rack.

As part of the process, a battery exchanger of the ultrasound utility station accepts a battery from an ultrasound machine and provide an additional battery to the ultrasound machine (502) and the ultrasound utility station charges the battery from the ultrasound machine using a battery charger (503). In some embodiments, the battery is manufactured by a different manufacturer than the manufacturer of the ultrasound machine itself.

The process may also include processing logic for determining the location of the ultrasound utility station using a location generator (504). In some embodiments, the location generator is implemented to determine the location of an ultrasound machine battery.

The process also includes processing logic for communicating one or more of the battery status of the battery, the ultrasound probe status of one or more ultrasound probes, and/or location of at least one of the ultrasound machine (505). In some embodiments, this communication is performed by a transceiver of the ultrasound utility station. In some embodiments, the transceiver is implemented to communicate the battery location to the ultrasound machine and/or a user device. In some embodiments, this communication occurs after the location generator determines the battery location of the battery.

The process may include the ultrasound utility station providing to an ultrasound machine at least one of an ultrasound gel bottle, a gel pack and a gel pad for transfer to the ultrasound machine (506) and providing for transfer to the ultrasound machine at least one of a needle kit, a peripheral intravenous kit, a nerve block kit, a cardiac kit, and a transesophageal echocardiogram kit, and an electrocardiogram kit (processing block 507). In one embodiment, these gel-related items and kits are provided by an ultrasound accessory dispenser of the ultrasound utility station. In one embodiment, the kits have a common mounting form and the ultrasound machine includes a mount configured to accept the common mounting form.

Figure 6:
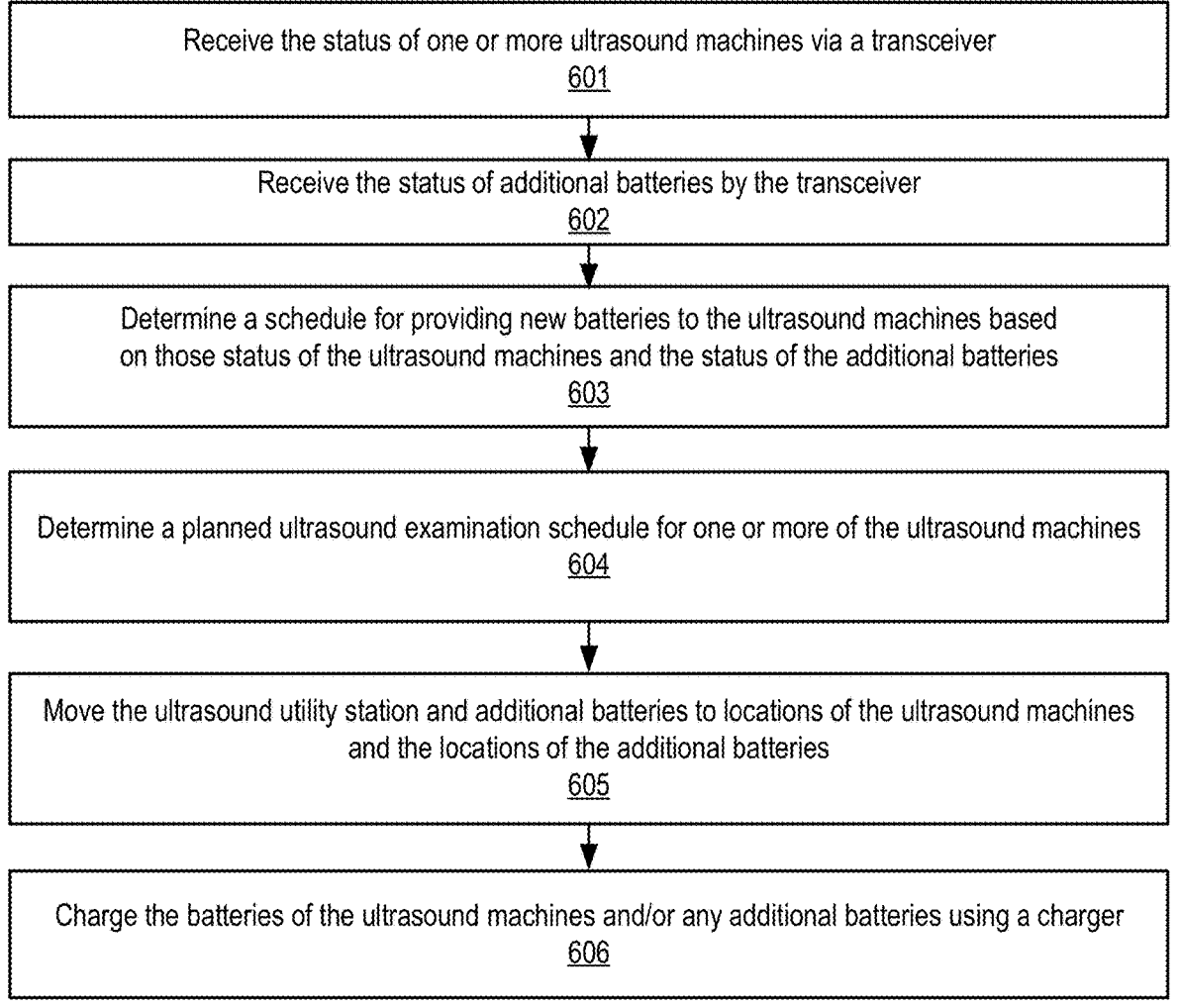
FIG. 6 illustrates a data flow diagram of one embodiment of a process performed by an ultrasound utility station.

FIG. 6 illustrates a data flow diagram of another embodiment of a process performed by an ultrasound utility station. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound utility station.

Referring to FIG. 6, in some embodiments, the process includes receiving the status of one or more ultrasound machines via a transceiver (processing block 601). In one embodiment, the status includes locations of the ultrasound machines in a care facility and the amounts of charged to the batteries of those ultrasound machines.

The process also includes processing logic for receiving the status of additional batteries by the transceiver (processing block 602). In some embodiments, this additional status includes the location of additional batteries in the care facility and the amounts of charge of those additional batteries.

The process also includes processing logic for determining a schedule for providing new batteries to the ultrasound machines based on those status of the ultrasound machines and the status of the additional batteries (processing block 603). In one embodiment, the schedule includes an order for providing one or more additional batteries to the ultrasound machines.

The process also includes determining a planned ultrasound examination schedule for one or more of the ultrasound machines (processing block 604). In some embodiments, the schedule is based on when the planned ultrasound examination is to occur. In some embodiments, this determination is made during a time window and is based on the amounts of charge of the batteries of the ultrasound machines.

In some embodiments, the process also includes moving the ultrasound utility station and additional batteries to locations of the ultrasound machines and the locations of the additional batteries (processing block 605) and charging the batteries of the ultrasound machines and/or any additional batteries using a charger (processing block 606). In some embodiments, moving the ultrasound utility station is performed by a location mechanism (e.g., motor, wheels, guidance system, etc.) of the ultrasound utility station.

There is a number of example embodiments described herein.

Example 1 is a method implemented by a computing device for configuring an ultrasound machine to be ready for use, where the method comprises: displaying, in a user interface of the computing device, a status of the ultrasound machine, where the status indicates a location of the ultrasound machine and an amount of charge of a battery of the ultrasound machine and displaying, in the user interface, an additional status of an ultrasound utility station, where the additional status indicating an additional location of the ultrasound utility station and available ultrasound probes on the ultrasound utility station. The method also includes: receiving, via the user interface, a first user input indicating a selection of an ultrasound probe of the available ultrasound probes; receiving, via the user interface, a second user input that determines a schedule for said configuring the ultrasound machine, the schedule indicating a time window and a charging location corresponding to the location, the additional location, or a user-selected location that is different from the location and the additional location; and instructing the ultrasound utility station to, during the time window and at the charging location, charge the battery of the ultrasound machine and provide the ultrasound probe for transfer to the ultrasound machine.

Example 2 is the method of example 1 that may optionally include instructing at least one of the ultrasound machine and the ultrasound utility station to move to the charging location.

Example 3 is the method of example 1 that may optionally include that the additional status indicates available accessory kits on the ultrasound utility station; and wherein the method further includes: receiving, via the user interface, another user input indicating a selection of an accessory kit of the available accessory kits; and instructing the ultrasound utility station to, during the time window and at the charging location, provide the accessory kit for transfer to the ultrasound machine.

Example 4 is the method of example 1 that may optionally include that the additional status indicates available gel-related accessories on the ultrasound utility station, the gel-related accessories including at least one of ultrasound gel bottle, a gel pack, and a gel pad; and the method further includes receiving, via the user interface, another user input indicating a selection of a gel-related accessory of the available gel-related accessories, and instructing the ultrasound utility station to, during the time window and at the charging location, provide the gel-related accessory for transfer to the ultrasound machine.

Example 5 is the method of example 1 that may optionally include receiving, via the user interface, another user input indicating a charge level for the battery, and instructing the ultrasound utility station to charge the battery to at least the charge level.

Example 6 is the method of example 1 that may optionally include that the additional status indicates cleanliness levels of the ultrasound machine and the available ultrasound probes.

Example 7 is the method of example 1 that may optionally include receiving, from the ultrasound utility station or the ultrasound machine and during the time window, a charging status of the battery, the charging status indicating one or more of a charge level of the battery and a time remaining to a full charge of the battery.

Example 8 is the method of example 1 that may optionally include communicating, to a manufacturer of the ultrasound machine or a manufacturer of the ultrasound utility station, at least one of the selection of the ultrasound probe, the schedule for said configuring the ultrasound machine, the status, and the additional status.

Example 9 is the method of example 1 that may optionally include receiving, from the ultrasound utility station and during the time window, a failure alert that indicates a charging failure for the battery and displaying, in the user interface, an indicator of the failure alert.

Example 10 is the method of example 1 that may optionally include that displaying, in the user interface, a map of a care facility, wherein the displaying the status of the ultrasound machine includes indicating the location of the ultrasound machine on the map and the displaying the additional status of the ultrasound utility station includes indicating the additional location of the ultrasound utility station on the map.

Example 11 is the method of example 1 that may optionally include receiving one or both of usage data and location data, the usage data indicating usage of the ultrasound machine and the location data indicating location of the ultrasound machine or the ultrasound utility station, and displaying, in the user interface, one or both of the usage data and the location data.

Example 12 is the method of example 1 that may optionally include receiving, via the user interface, a third user input indicating a selection of the ultrasound machine for use by a user.

Example 13 is an ultrasound utility station to configure an ultrasound machine to be ready for use, the ultrasound utility station including: a battery exchanger configured to accept a battery from the ultrasound machine and provide an additional battery for the ultrasound machine; a battery charger configured to charge the battery from the ultrasound machine; and a probe rack configured to house ultrasound probes that can be coupled to the ultrasound machine. The ultrasound utility station also includes a location generator configured to determine a location of the ultrasound utility station; and a transceiver configured to communicate one or more of a battery status of the battery, a battery status of the additional battery, an ultrasound probe status of one or more of the ultrasound probes, and the location to at least one of the ultrasound machine and a user device.

Example 14 is the ultrasound utility station of example 13 that may optionally include a gel dispenser implemented to provide, for transfer to the ultrasound machine, at least one of ultrasound gel bottle, a gel pack, and a gel pad.

Example 15 is the ultrasound utility station of example 13 that may optionally include an ultrasound accessory dispenser implemented to provide, for transfer to the ultrasound machine, at least one of a needle kit, a peripheral intravenous kit, a nerve block kit, a cardiac kit, a transesophageal echocardiogram kit, and an electrocardiogram kit, wherein the needle kit, the peripheral intravenous kit, the nerve block kit, the cardiac kit, the transesophageal echocardiogram kit, and the electrocardiogram kit have a common mounting form, and the ultrasound machine includes a mount configured to accept the common mounting form.

Example 16 is the ultrasound utility station of example 13 that may optionally include that one or more of the ultrasound probes are implemented to wirelessly communicate to the ultrasound machine and include a rechargeable probe battery, and the probe rack is implemented to charge the rechargeable probe battery.

Example 17 is the ultrasound utility station of example 13 that may optionally include that the probe rack includes a cleaning vessel that contains a cleaning agent to clean the ultrasound probes when the ultrasound probes are housed by the probe rack.

Example 18 is the ultrasound utility station of example 13 that may optionally include that the location generator is implemented to determine a battery location of the battery, and the transceiver is implemented to communicate the battery location to one or both of the ultrasound machine and the user device.

Example 19 is the ultrasound utility station of example 13 that may optionally include that the battery is implemented to provide power to at least one additional ultrasound machine manufactured by a different manufacturer than a manufacturer of the ultrasound machine.

Example 20 is the ultrasound utility station of example 13 that may optionally include that the transceiver is implemented to receive, from the ultrasound machine, an indicator of a location of the ultrasound machine.

Example 21 is an ultrasound utility station including: a transceiver configured to receive statuses of ultrasound machines, the statuses including locations of the ultrasound machines in a care facility and amounts of charge of batteries of the ultrasound machines, where the transceiver is configured to receive additional statuses of additional batteries, the additional statuses including locations of the additional batteries in the care facility and amounts of charge of the additional batteries. The ultrasound utility station also includes a scheduler configured to determine, based on the statuses and the additional statuses, a schedule for providing the additional batteries to the ultrasound machines, the schedule including an order of the ultrasound machines and times for said providing.

Example 22 is the ultrasound utility station of example 21 that may optionally include an examination planner implemented to determine, over a time window based on the amounts of charge of the batteries of the ultrasound machines, planned ultrasound examinations scheduled for the ultrasound machines, wherein the scheduler is implemented to determine the schedule based on the planned ultrasound examinations.

Example 22 is the ultrasound utility station of example 21 that may optionally include a charger implemented to charge the batteries and the additional batteries; a locomotion mechanism implemented to move the ultrasound utility station to the locations of the ultrasound machines and the locations of the additional batteries; and a transfer mechanism implemented to remove the batteries from the ultrasound machines and transfer the additional batteries to the ultrasound machines.

Example 24 is the ultrasound utility station of example 21 that may optionally include a neural network implemented at least partially in hardware of the ultrasound utility station to generate a map of the care facility.

Example 25 is the ultrasound utility station of example 24 that may optionally include that the map indicates the locations of the ultrasound machines.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. An ultrasound apparatus comprising:
a charging station; and
a display device, wherein the charging station is configured to charge a battery of a first ultrasound machine, the charging station comprising a first module to be attached to a charging location and a second module to be attached to the first ultrasound machine, wherein the first module includes a first circuitry and one or more sensors coupled to the first circuitry and the second module includes a second circuitry, wherein the first circuitry and the second circuitry are implemented to wirelessly communicate to each other and to transfer power from the charging location to the battery of the first ultrasound machine via at least one of an inductive power transfer or a RF power transfer, and wherein the one or more sensors are configured to generate sensed data to determine a distance and a direction that the first ultrasound machine is moved; and a processor coupled to the charging station and configured to generate a map of a care facility that indicates locations of the first ultrasound machine and the charging station to display on the display device based on the sensed data, wherein the processor is further configured to: receive a charging station status including a first status indicating that the charging station is currently charging other ultrasound machine and is not available to charge the first ultrasound machine and a second status indicating that the charging station is currently not charging the other ultrasound machine and is available to charge the first ultrasound machine; and display the charging station status on the display device.

2. The ultrasound apparatus as described in claim 1, further comprising
a battery exchanger configured to receive the battery for the first ultrasound machine.

3. The ultrasound apparatus as described in claim 1, further comprising
a probe rack configured to house one or more ultrasound probes to be coupled to the first ultrasound machine.

4. The ultrasound apparatus as described in claim 1, wherein the first module is to be attached to the charging location on at least one of a wall or a floor.

5. The ultrasound apparatus as described in claim 1, wherein the second module is movable relative to the first module.

6. The ultrasound apparatus as described in claim 1, wherein the first module includes one or more electronic charging indicators.

7. The ultrasound apparatus as described in claim 1, wherein the first module is a charging mat.

8. The ultrasound apparatus as described in claim 1, wherein at least one of the first module or the second module is configured to generate an alert to indicate at least one of a charging status, a charging failure, or a position of the second module relative to the first module.

9. The ultrasound apparatus as described in claim 1, wherein the first module includes one or more indicators to indicate an area to place the first ultrasound machine.

10. The ultrasound apparatus as described in claim 1, wherein the first module includes a first transceiver and the second module includes a second transceiver to wirelessly communicate with the first transceiver.

11. An ultrasound apparatus for a first ultrasound machine, comprising:
a display device;
a first wireless module including a first circuitry and one or more sensors coupled to the first circuitry that is configured to be connected to a charging location; and
a second wireless module including a second circuitry that is configured to be attached to the first ultrasound machine, wherein the first wireless module and the second wireless module are implemented to communicate to each other via a wireless communication link to place the first ultrasound machine in a proximity of the charging location and to transfer power via at least one of an inductive power transfer or an RF power transfer from the first circuitry to the second circuitry to charge a battery of the first ultrasound machine, and wherein the one or more sensors are configured to generate sensed data to determine a distance and a direction that the first ultrasound machine is moved; and a processor coupled to the charging station and configured to generate a map of a care facility that indicates locations of the first ultrasound machine and the charging station to display on the display device based on the sensed data, wherein the processor is further configured to: receive a charging station status including a first status indicating that the charging station is currently charging other ultrasound machine and is not available to charge the first ultrasound machine and a second status indicating that the charging station is currently not charging the other ultrasound machine and is available to charge the first ultrasound machine; and display the charging station status on the display device.

12. The ultrasound apparatus as described in claim 11, wherein the first wireless module includes one or more indicators to indicate an area to place the first ultrasound machine.

13. The ultrasound apparatus as described in claim 11, wherein the first wireless module includes a first transceiver that is implemented to receive an indicator of a location of the first ultrasound machine and the second wireless module includes a second transceiver to wirelessly communicate with the first transceiver.

14. The ultrasound apparatus as described in claim 11, wherein the first wireless module is to be attached to the charging location on at least one of a wall or a floor.

15. The ultrasound apparatus as described in claim 11, wherein the first wireless module has one or more first marks to align with the second module.

16. The ultrasound apparatus as described in claim 11, wherein the first wireless module includes one or more electronic charging indicators.

17. The ultrasound apparatus as described in claim 11, wherein at least one of the first wireless module or the second wireless module is configured to generate an alert to indicate at least one of a charging status, a charging failure, or a position of the second wireless module relative to the first module.

\* \* \* \* \*